(12) United States Patent
Hurst

(10) Patent No.: US 11,309,064 B2
(45) Date of Patent: Apr. 19, 2022

(54) INDIVIDUALIZED DOSING TECHNIQUE WITH MULTIPLE VARIABLES

(71) Applicant: Katherine L. Hurst, Coralville, IA (US)

(72) Inventor: Katherine L. Hurst, Coralville, IA (US)

(73) Assignee: Katherine L. Hurst, Coralville, IA (US)

( * ) Notice: Subject to any disclaimer, the term of this patent is extended or adjusted under 35 U.S.C. 154(b) by 700 days.

(21) Appl. No.: 15/675,448

(22) Filed: Aug. 11, 2017

(65) Prior Publication Data

US 2017/0344723 A1    Nov. 30, 2017

(51) Int. Cl.
| | | |
|---|---|---|
| *G16H 10/20* | (2018.01) | |
| *G16H 10/60* | (2018.01) | |
| *G16H 20/10* | (2018.01) | |

(52) U.S. Cl.
CPC .............. *G16H 10/20* (2018.01); *G16H 10/60* (2018.01); *G16H 20/10* (2018.01)

(58) Field of Classification Search
CPC ................................ G06Q 50/00; G06F 19/00
USPC ........................................................ 705/2, 3
See application file for complete search history.

(56) References Cited

U.S. PATENT DOCUMENTS

| | | | | |
|---|---|---|---|---|
| 7,739,130 B2 * | 6/2010 | Surwit | ................ | G06F 19/3418 705/3 |
| 2009/0216561 A1 * | 8/2009 | Woo | ........................ | G16H 20/10 705/3 |
| 2009/0234674 A1 * | 9/2009 | Wurster | ................. | G06Q 10/10 705/3 |
| 2012/0072231 A1 * | 3/2012 | Mayer | .................... | G16H 20/10 705/2 |

OTHER PUBLICATIONS

Google patents search, Mar. 25, 2020 (Year: 2020).*
ip.com search.*

* cited by examiner

*Primary Examiner* — Dilek B Cobanoglu
(74) *Attorney, Agent, or Firm* — Kirk Hahn

(57) ABSTRACT

A method to quantify and correct for drug-drug interaction, physiologic change, diet, weight, genetic data and compliance on Warfarin dosing. The International Normalized Ratio (INR), a lab value used to follow Warfarin use, will fluctuate in an unpredictable manner due to factors other than the current Warfarin dose. The method mathematically describes these changes and eventually adjusts for these interacting factors through the use of logistic regression (LR) or multiple linear regression analysis. By anticipating changes in INR, Warfarin dosing can be adjusted resulting in patients having their INR be therapeutic range. The technique can be used in any field that requires a specific measured quantity, with variables that change and the need to correct for changes with a mathematical model.

19 Claims, 10 Drawing Sheets

INDIVIDUALIZED DOSING TECHNIQUE WITH MULTIPLE VARIABLES

This application is a Continuation application of and claims priority to U.S. Non-Provisional application Ser. No. 13/344,752, filed on Jan. 6, 2012; the contents of which is herein incorporated by this reference in its entirety. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

Pharmaceutical products have become ubiquitous with people taking drugs everyday for long periods. These drugs become a daily routine and allow a patient to have a normal and productive life. They may offer the only answer for some life-threatening conditions, such as, high blood pressure, diabetes, and high cholesterol. However, the great benefits of these drugs can be overshadowed by unknown and unforeseen complications, and interactions between the drugs. Therefore, doctors must consider the combination of drugs each patient is taking before prescribing a new drug for a new ailment.

Unfortunately, the side-effects from the various combinations of drugs may be unique to that person and may have never been seen before. The onset and severity of side effects may be related to the dosage, length of time on the drug, type of drug being taken, as well as, what other drugs are being taken at the same time and life style issues (e.g., obesity, smoking, alcohol consumption) of the patient.

These issues are compounded by the ever changing daily consumption of over the counter drugs (e.g., pain killers, sleeping pills), herbal teas, cough medicine and other products that may not even be considered by the patient has having any effect on their health.

A complex amalgamation of products must be considered by the physician every time a patient complains about an ailment and a treatment is proposed for the patient. A typical physician is unable to know all the complications that may arise from each combination of factors. A case in point is the difficult task of prescribing anticoagulants for patients with risk factors for strokes and heart disease. Anticoagulants can be difficult medications to manage due to a very complex pharmacology. Many factors affect anticoagulation therapy, for example, genetic factors, age, sex, diet, drug interactions, and illness, as well as patient compliance with recommended dosing schedules.

Warfarin (also known under the brand names Coumadin, Jantoven, Marevan, Lawarin, Waran, and Warfant) is a medication indicated for the treatment of blood clots and abnormal heart beats, such as, atrial fibrillation (AF).

Warfarin is a vitamin K antagonist that interferes with the vitamin K conversion cycle. Biologically active coagulation factors are produced by adding carboxyl groups during the vitamin K conversion cycle. Warfarin's action causes a decrease in the activity of reductase in the cycle, which causes a reduction in the number of added carboxyl groups. This results in partially carboxylated or completely decarboxylated vitamin K-dependent clotting factors (II, VII, IX, X) with reduced procoagulant activity.

Additionally, pharmaceutical Warfarin in the US is a racemic mixture of the S-(−)- and R-(+)-enantiomers. The 2 enantiomers of Warfarin have different half-lifes and potencies. The R-enantiomer has a half-life almost twice as long as the S-enantiomer; however, the S-enantiomer is 3 to 5 times more potent than the R-enantiomer. The 2 enantiomers also have different metabolic pathways. The R-enantiomer is reduced to an alcohol and hydroxylated at the 6-position and the S-enantiomer is hydroxylated form a 7-hydroxyWarfarin.

Drugs that either inhibit or induce Cytochrome P450 isoenzyme 2C9 affect Warfarin concentrations by enhancing or reducing the pharmacologic effect. The metabolism of R-enantiomer involves Cytochrome P450 isoenzymes A2, 2C19, and 3A and ketoreductases. Inhibition of these isoenzymes, which causes an increase of the R-enantiomer, has little effect on anticoagulant activity of Warfarin due to its lower potency.

Pharmacogenetics has been utilized to increase understanding of individualized dosing of Warfarin. Genetic tests have identified Cytochrome P450 2CP as a major enzyme in Warfarin metabolism. Polymorphisms produce variants in catalytic properties of the breakdown of Warfarin's more potent S enantiomer. However, genetic testing is expensive and does not offer a long term solution to dosing with the presence of concurrent interacting medications. A patient's gene status may initially be helpful with the first Warfarin dose; however, it does not address the most challenging aspect of Warfarin dosing, drug-drug, drug-food, and drug-alcohol interactions.

There are many drug-drug interactions observed with Warfarin due to the different pharmacokinetic and pharmacodynamic properties of Warfarin and the other coumarins. In general, from a pharmacokinetic perspective, anything that reduces absorption of Warfarin will reduce its activity and anything that inhibits binding to its protein-binding sites will increase unbound Warfarin, although this will be offset by increased metabolism of unbound Warfarin.

Metabolism of Warfarin takes place in the liver. Cytochrome P450 isoenzymes [2C9, 2C19, 2C8, 2C18, 1A2, and 3A4] and hepatic reductases are involved in Warfarin's metabolism. Isoenzyme 2C9 is very important in this process since it has been shown to specifically serve as 7-hydroxylase, and to a lesser extent 6-hydroxylase, of S-enantiomer. This isoenzyme is believed to be responsible for the clearance of most S-enantiomer.

Patients with nonvalvular AF have at least a 5-fold increased risk for stroke and those with valvular AF have an estimated 17-fold increased risk for stroke. Numerous randomized controlled studies of Warfarin therapy have conclusively demonstrated that long-term anticoagulation therapy can reduce the risk for ischemic stroke by approximately 68% in patients with nonvalvular AF, and even more in patients with valvular AF.

Despite conclusive evidence demonstrating the benefit of blood clot prevention, practice pattern evaluations of prescribing physicians consistently identify suboptimal use of Warfarin. Warfarin still is not prescribed to most patients with AF even though therapy is highly cost-effective in the prevention of stroke. Physicians report difficulty in maintaining therapy within the therapeutic range. However, additional training, availability of consultant advice, or guidelines on managing anticoagulation therapy would increase the willingness to use it.

Proper outpatient dosing of Warfarin remains a challenge for primary care providers. Studies show poor use of the medication in an outpatient setting. Less than 50% of patients are within therapeutic range [INR value 2-3].

Patients with an INR below 2 are at risk for clots and patients with an INR above 3 are at risk of bleeding. Patients' understanding of the risks and benefits of the therapy is low in elderly patients, a population with high rates of AF.

The risk of major hemorrhage ranges from 1.2 to 7 episodes per 100 patients in cohort studies. The risk of a major hemorrhage increases cumulatively as the duration of therapy increases. The challenge in an outpatient setting is to increase anticoagulation control and have patients remain in therapeutic INR range, which requires a better understanding of individual patient responses to Warfarin therapy.

Pharmacodynamic interactions are also possible when Warfarin is combined with other drugs that interfere with platelet aggregation or synthesis of clotting factors; or drugs affecting the metabolism of clotting factors (e.g., thyroid compounds), or drugs leading to vitamin K deficiency (e.g., altered gut flora, interference with absorption or metabolism of vitamin K) to produce a synergistic effect.

It has been found that the sensitivity to Warfarin increases with age.

Acute alcohol intake affects the activity of Warfarin and may increase anticoagulation by decreasing Warfarin metabolism. However, chronic alcohol ingestion has the opposite effect by decreasing anticoagulation due to increased Warfarin metabolism. The anticoagulant effect of Warfarin is severely changed by even small amounts of alcohol. A patient taking Warfarin who ingests a few drinks may experience anticlotting effects stronger than expected for their medical purposes, which will place the person at risk for increased bleeding.

Alcohol inhibits the metabolism of Warfarin by Cytochrome P450 in the liver, which allows the Warfarin to remain in the body for a longer period. However, the activity of Cytochrome P450 in the liver is actually increased by chronic alcohol consumption, which in turn increases the metabolism of Warfarin and reducing the amount in the body. This reduction of Warfarin in the body then requires higher doses to achieve the needed anticoagulant effect.

This observed effect on the Warfarin dose points out the need to take into account both small amounts of alcohol use and chronic use of alcohol, since they have opposite effects, both of which have serious ramifications for the patient.

Antibiotics, depending on the type, have different mechanisms that affect the drug-drug interactions with Warfarin. Penicillin-type drugs are believed to enhance Warfarin by decreasing gut flora that produces vitamin K, which causes a vitamin K deficiency.

Warfarin has been shown to have a drug interaction with amoxicillin/clavulanate potassium which causes the INR to be elevated over the same dose of Warfarin without amoxicillin/clavulanate potassium. An increased INR due to the Warfarin interaction with antibacterial agents must be considered which prescribing a therapeutic dose to a patient to prevent unexpected bleeding episodes.

Due to both its pharmacokinetic and pharmacodynamic characteristics, there are many drug-drug, drug-herb, and drug-food interactions (Table 1).

TABLE 1

| Drug | Effect on Warfarin activity |
| --- | --- |
| macrolides [Clarithromycin Dirithromycin Erythromycin Roxithromycin Telithromycin] | Inhibits Vitamin K gut flora, inhibits Cytochrome system, competitively bind plasma proteins and thereby displacing Warfarin from the binding sites producing higher concentration of free Warfarin, slowing Warfarin clearance |
| Metronidazole | Potentates the actions of Warfarin, inhibits the activity of the enzyme responsible for oxidation of Warfarin. |
| Ciprofloxacin | Potentates the actions of Warfarin, inhibits Cytochrome P450 |
| Teicoplanin | Produces Warfarin resistance and enhances Warfarin clearance thereby reducing its effect |
| Anorexia, vomiting | Reduces intake of Vitamin K, potentates Warfarin |
| Ibuprofen | Causes clinical problems in some patients treated with Warfarin, particularly in the elderly on complex drug regimens |
| D-003 is a mixture of higher aliphatic primary acids isolated and purified from sugarcane wax, the main component of which is octacosanoic acid. | Combined therapy of minimally effective doses of D-003 and Warfarin produces an antithrombotic effect significantly higher than those produced by each monotherapy. Prolongs bleeding time induced by Warfarin and simultaneous administration of D-003. Shows a synergistic effect between both drugs |
| Azathioprine or mercaptopurine, phenprocoumon. | Reduces Warfarin and acenocoumarol activity. Increased Warfarin dosages may be necessary. Approximately a three-fold increase in the anticoagulant dosage when taking Azathioprine or mercaptopurine. |
| paclitaxel and etoposide | Highly protein bound. Interacts with other protein-bound drugs (e.g., Warfarin). Increases INR |
| chemotherapy agents | Inhibits Cytochrome P450 |
| Gemcitabine, 5-FU and capecitabine | Increases INR. Reduces requirement for Warfarin. |
| Tamoxifen | Tamoxifen and Warfarin are highly protein bound. Tamoxifen displaces Warfarin from proteins and increases the concentration of free Warfarin. Use of Tamoxifen with Warfarin is contraindication since it increases the level of anticoagulation and risk of bleeding complications |

Currently several new drugs that are direct inhibitors of factor Xa are being tested. These drugs, Xa inhibitors, inhibit a key protein in forming blood clots, and are thought to have no drug-drug interactions and patients do not need to keep track of their INR. Some people feel these direct Xa inhibitors may eventually replace Warfarin; however, Warfarin has been used for over 50 years with strong data to support the efficacy and cost-effectiveness. Also there is no quick way to reverse the Xa inhibitors with an anecdote in the case of trauma or emergent surgery. This fact can place all patients on Xa inhibitors at risk for potentially life threatening bleeding episodes.

Warfarin inhibits a lot of other proteins, besides factor Xa, from forming a clot. Additionally, it is rapidly reversible with vitamin K and, in more serious situations, fresh frozen plasma. The adverse effect profile of Warfarin is well known and understood. If a direct competitor of Warfarin comes into the market it would have to compete with a medication that costs as low as $41.00 dollars a year with a well known and understood drug profile.

Previous attempts at solving these dosing problems have not been successful in addressing the important issues; including guarding patients' medical records, specific drug-drug interactions of each patient, and predicting future effects of novel pharmaceutical products.

There have been some attempts to develop methods to simplify the calculation of the Warfarin dose; however, the previous attempts have not taken an individualized approach to the calculation for a specific patient.

For example, Woo et al. (US 20090216561) discloses methods for determining dosages of anticoagulants for a patient. The method includes inputting (a) the patient's cumulative dose of anticoagulant from a previous time period, (b) the patient's current INR, (c) an INR target, and (d) current anticoagulant pill size, into a series of equations; determining a new dose allocated for a next time period, chosen from a preselected list of doses ranging from a minimum dose to a maximum dose for the anticoagulant pill size; and providing the new allocated dose.

However, this method only considers the cumulative dose of Warfarin over the previous time period (e.g. 1 week) and the current INR value. The method does not consider the daily dose of Warfarin or other drugs taken during the period before the current INR was taken. The method only considers the current INR value and assumes a direct relationship between INR and cumulative amount of Warfarin. If the INR is 20% too high above the goal INR, then the cumulative amount of Warfarin is reduced by 20%. Also, the method is always looking "back" to determine the Warfarin dose in the future.

The method in Woo '561 does not consider any other factors except INR and cumulative dose of Warfarin. Nor does it consider that there may be individual variations in the effects of other factors by a patient.

Woo '561 discloses equations to determine the Warfarin dose, however, the equations only use the observed INR in the patient, rather than trying to compare the observed INR with a predicted INR. Woo '561 uses hindsight in the hope of predicting future events and the equations are based on cumulative Warfarin rather than individual factors.

The point of Woo '561 is to correct the problem that while some protocols for anticoagulant dose management can adjust a dose; such methods do not allocate the doses over a time period for optimal use. These systems fall short in that they rely on one dose, and they do not allocate doses over a time period.

Woo '561 assumes all factors are identical so the only variable is INR and it is used to change the amount of Warfarin. It does not look at individual factors that may affect INR to modify doses to reflect these factors.

Another attempt at solving the problems associated with anticoagulant therapy was disclosed by Surwit (U.S. Pat. Nos. 7,739,130; 6,980,958; 6,589,169; 6,024,699; and US 20110077971). This family of patents and applications discloses methods and apparatuses to receive and analyze information regarding a patient's compliance with taking their anticoagulation medication and testing their INR. These methods include the self-recording of personal and medical information during the day-to-day activities of the patient. However, this information is not used to analyze its effect on future INR results, but to give warnings of potential medical issues of an immediate under- or over-medication of anticoagulant drugs. The disclosed algorithm in Surwit is used to modify the dose of Warfarin and frequency of taking the dose to correct the immediate medical issues associated with the under- or over-medication.

The goal of the disclosed method and apparatus in Surwit is to allow the remote self-monitoring of the anticoagulant therapy. Additionally, the apparatus uses alarms to initiate specific tasks by the patient. The disclosed system monitors, diagnoses, and treats medical conditions of remotely located patients. Remote portable patient monitors are configured to establish communications directly with a central data processing system with communications links. The monitor may incorporate physician-prescribed algorithms for calculating medicine dosages or implement a medication dosage algorithm for anticoagulation therapy based on values communicated to the data processing center by the monitor and communicate the results directly to the patient.

Patients are responsible for self-recording data into the apparatus and transmitting the data to a data processing center on a regular basis. Although the apparatus assesses changes in a patient's diet, medication, illness, or vitamins, these changes are only "flagged" for a possible telephone call after the next data transmission. However, these changes are not assessed quantitatively by the apparatus, only identified qualitatively. Interactions are noted but not the severity of the interaction nor whether it is a positive or negative interaction or whether it is synergistic.

Therefore the general concept of Surwit is that a patient undergoing anti-coagulation therapy logs onto his/her personal monitor according to a predefined schedule (for example, a daily schedule). If the monitor determines that information (or data) regarding the patient's Warfarin and PT test regimens [INR test by a health care professional] (or other aspects of the anticoagulation therapy) are missing or insufficient, the monitor initiates a procedure for obtaining the missing patient data. The disclosed method of monitoring a disease therapy of a patient includes a patient-administered medication regimen and a patient-administered regimen for a test that monitors efficacy of the medication regimen.

Another attempt at solving the problems associated with anticoagulant therapy has used a qualitative methods or quasi-quantitative methods to modify the anti-coagulation therapy. The qualitative methods are not very useful in maintaining a uniform and consistent INR value for patients. Although, these methods appear to evaluate the many variables affecting the ultimate result from a specific dose of anti-coagulant drug, they lack the specificity, reliability, and repeatability needed to maintain a patient on anti-coagulation therapy without having medical issues that affect the well-being or life of a patient.

The quasi-quantitative methods appear to use mathematical equations or algorithms to calculate a new dosage at each patient's visit, but they are little more than the qualitative methods. For example, several methods involve the use of an equation to modify the dose after a new INR reading. However, the equations are usually simply reflecting the change in the INR to the change in the dose or are used to calculate the frequency of intake and amount of a weekly dose to arrive at weekly therapy regime.

Another example of a quasi-quantitative method is Wurster US 20090234674. The disclosed method in Wurster '674 calculates a weekly Warfarin dose and converts the total weekly requirement into daily dosages based on the number of milligrams in the pills selected for treatment. Additionally, Wurster '674 discloses using a comprehensive list of medical issues to facilitate a logical manner of treatment by doctors; however, the information is qualitative in nature and each medical issue is not evaluated in a quantitative, statistical significant matter to give repeatable and reliable results for basing a medical decision.

In contrast, as will be seen in the Detailed Description of the Invention and Examples, the disclosed systems, processes, methods and apparatuses use quantitative data to obtain statistically significant results, which are used to develop an individual equation for each patient to determine doses of anticoagulant drug that will give specific, reliable, and repeatable INR results. Additionally, the data is modified in relation to the specific results for each patient to develop an individualized equation that takes into account the specific effects of each factor for that patient.

The idea of considering and trying out variables for each factor that may affect the INR has not previously been disclosed.

BRIEF SUMMARY OF THE INVENTION

The present application focuses on the critical factors that affect the calculation for the dose of an anticoagulant and identifies the factors that are critical to each individual patient and their relative affect to that individual patient. The present application uses quantitative methods to consider the effect of daily factors on the activity of the anti-coagulate drug. The disclosed methods calculate the daily dose of anti-coagulate drug to maintain a goal INR.

Additionally, the disclosed methods look at the current INR and the quantitative effects of the various daily life factors to determine a daily dose of anti-coagulate drug to obtain a predicted INR in the future. The quantitative value of each factor is modified to obtain an individualized value for each patient, so the equation becomes more reliable in predicating future INR as the values become more representative of that individual patient.

In one embodiment of the disclosed systems, processes, methods and apparatuses; a mathematical model is employed that uses Logistic regression to help maintain a therapeutic INR. Health care professionals with patients taking several medications that potentially interfere with Warfarin will benefit from the disclosed processing, methods and apparatuses. The constructed and validated predictive model software guides the patient's Warfarin dose. The initial baseline data base consists of INR, Warfarin, personal patient data, drug-drug interactions and other factors compiled over time from a large number of patients. These initial default values are used for the first prediction of a Warfarin dose. During successive visits by the patient, these default values are changed automatically by the mathematical model to represent the specific interactions and inter-relationships observed in that patient. Therefore, the mathematical model generates a unique model for each patient with individualized values for each parameter in the model.

In one embodiment of the disclosed systems, processes, methods and apparatuses; specific data is collected from a patient interaction with a health care professional.

In one embodiment of the disclosed systems, processes, methods and apparatuses; data is stored in a secure database that is Health Insurance Portability and Accountability Act (HIPAA) [a federal law to protect patient's privacy] approved and managed by health care professionals.

In one embodiment of the disclosed systems, processes, methods and apparatuses; specific data, in a digital format, is used for each patient and one equation is used per patient.

In one embodiment of the disclosed systems, processes, methods and apparatuses; drug-drug interactions are quantified, doses are correct for the drug-drug interaction, and dosing is based on the drug-drug interaction.

In one embodiment, the disclosed systems, processes, methods and apparatuses can be used to dose any drug or treatment that requires a dynamic system to consider multiple variables that change over time, interact with each other and interact with body systems at times of fever, liver failure, diet changes and loose stools.

In one embodiment of the disclosed systems, processes, methods and apparatuses; information (vital signs, drug-drug interaction, questions about fever, diarrhea, diet and current dose) is collected, stored and used to calculate doses of medication.

In one embodiment of the disclosed systems, processes, methods and apparatuses; the INR variable is stored as the Y value and the current dose of Warfarin is stored as the X value in a logistic equation.

In one embodiment of the disclosed systems, processes, methods and apparatuses; a unique equation is used for each patient.

In one embodiment of the disclosed systems, processes, methods and apparatuses; a large database and general equation is used to obtain coefficients, when necessary, for new drugs, conditions or life style issues.

In one embodiment of the disclosed systems, processes, methods and apparatuses; the dosing or output is stored as a percent chance of being in this INR range based on the past data using this daily dose.

In one embodiment of the disclosed systems, processes, methods and apparatuses; a percent is stated of being in therapeutic INR range, which is a Y value and a mathematical guided dosage recommendation.

In one embodiment of the disclosed systems, processes, methods and apparatuses; an equation is used to anticipate future INR when a new pharmaceutical product (e.g. diuretic or antibiotic) is proposed for use.

In one embodiment of the disclosed systems, processes, methods and apparatuses; the equation with a velocity [i.e., change in lab value divided by time] and time needed to go back to normal INR or time needed at a certain dose to reach therapeutic INR In one embodiment of the disclosed systems, processes, methods and apparatuses; the information is output by digital or verbal means, but guided by a health care provider In one embodiment of the disclosed systems, processes, methods and apparatuses; two equations are used: 1) a patient specific equation that is the result of the patient's readings over time and 2) a large population mixed study equation that has data from a large number of patients.

In one embodiment of the disclosed systems, processes, methods and apparatuses; a dosing scheme is used that is universal to all drugs and can be used with any type of interface that is HIPAA approved, respects patient privacy, and run by health care professionals that are licensed to practice medicine.

In one embodiment of the disclosed systems, processes, methods and apparatuses; a printout, audible read out, electronic display, or any combination thereof may be used to disclose the new dose of anti-coagulant.

In one embodiment of the disclosed systems, processes, methods and apparatuses; individual factors specific to the patent are used, which may include genetic factors, age, sex, diet, drug interactions, illness, patient compliance with prior dosing schedules, or any combination thereof, into the series of equations.

In one embodiment of the disclosed systems, processes, methods and apparatuses; patient information is obtained and recorded digitally in a binary variable outcome, 1=yes, 0=no, in a secure database.

In one embodiment of the disclosed systems, processes, methods and apparatuses; a mathematical model is used, for example, a logistic or multiple linear regressions to analyze variables.

In one embodiment of the disclosed systems, processes, methods and apparatuses; each patient's individual equation is tested for validity using a mathematical technique, such as, likelihood ratio [i.e., the probability of a clinical finding in patients with disease divided by the probability of the same finding in patients without disease].

In one embodiment of the disclosed systems, processes, methods and apparatuses; the significance of each variable is tested with a mathematical test, such as, Wald test [e.g., a technique to test the significance of explanatory variables in a statistical model].

In one embodiment of the disclosed systems, processes, methods and apparatuses; if a variable is found to be not mathematically significant, it is excluded from the equation.

In one embodiment of the disclosed systems, processes, methods and apparatuses; if a variable is found to be mathematically significant, it is included in the equation.

In one embodiment of the disclosed systems, processes, methods and apparatuses; a mathematical coefficient is used to represent or quantify any drug-drug, drug-food, drug-alcohol, drug-fever, drug-activity, and other drug interactions to quantitatively determine an individual factor or cumulative factors effect.

In one embodiment of the disclosed systems, processes, methods and apparatuses; a mathematical coefficient is used to represent or quantify any drug-drug, drug-food, drug-alcohol, drug-fever, drug-activity, and other drug interactions to quantitatively determine the effect of individual factors and cumulative factors, including increased activity, decreased activity and synergistic activity (either increased or decreased) of the prescribed drug.

In one embodiment of the disclosed systems, processes, methods and apparatuses; genetic information is obtained and recorded for current and future dosing.

In one embodiment of the disclosed systems, processes, methods and apparatuses; a measurement of liver function is obtained and recorded for current and future dosing.

In one embodiment of the disclosed systems, processes, methods and apparatuses; a measurement of kidney function is obtained and recorded for current and future dosing.

In one embodiment of the disclosed systems, processes, methods and apparatuses; a goal INR is obtained and recorded.

In one embodiment of the disclosed systems, processes, methods and apparatuses; a diagnosis for Warfarin need is obtained and recorded.

In one embodiment of the disclosed systems, processes, methods and apparatuses; ethnic information is obtained and recorded for current and future dosing.

In one embodiment of the disclosed systems, processes, methods and apparatuses; gender information is obtained and recorded for current and future dosing.

In one embodiment of the disclosed systems, processes, methods and apparatuses; age of patient in years and months is obtained and recorded for current and future dosing.

In one embodiment of the disclosed systems, processes, methods and apparatuses; weight of patient in kilograms is obtained and recorded for current and future dosing.

In one embodiment of the disclosed systems, processes, methods and apparatuses; information (name, dose, frequency of intake, duration, and reason for taking medication) for each medication prescribed to the patient by any doctor or medical practitioner is obtained and recorded at the time of each visit.

In one embodiment of the disclosed systems, processes, methods and apparatuses; any changes in dosage or route of medication prescribed to the patient by any doctor or medical practitioner is obtained and recorded at the time of each visit.

In one embodiment of the disclosed systems, processes, methods and apparatuses; the amount of alcohol taken on a regular basis or anticipated to be taken in the future is obtained and recorded for current and future dosing.

In one embodiment of the disclosed systems, processes, methods and apparatuses; the amount and frequency of eating vitamin K containing food is obtained and recorded for current and future dosing.

In one embodiment of the disclosed systems, processes, methods and apparatuses; an estimated percent compliance of previous prescribed anticoagulant therapy is obtained and recorded at the time of each visit.

In one embodiment of the disclosed systems, processes, methods and apparatuses; menopause status in female patients is obtained and recorded.

In one embodiment of the disclosed systems, processes, methods and apparatuses; the number of instances of fevers since the last visit is obtained and recorded at the time of each visit.

In one embodiment of the disclosed systems, processes, methods and apparatuses; the number of episodes of diarrhea since last INR reading is obtained and recorded at the time of each visit.

In one embodiment of the disclosed systems, processes, methods and apparatuses; the amount and type of herbal medicines taken since last visit is obtained and recorded at the time of each visit.

In one embodiment of the disclosed systems, processes, methods and apparatuses; the number of falls since last INR recording number of falls is obtained and recorded at the time of each visit.

In one embodiment of the disclosed systems, processes, methods and apparatuses; the quantity and type of cigarettes, cigars and pipe tobacco smoked since last INR reading is obtained and recorded at the time of each visit.

In one embodiment of the disclosed systems, processes, methods and apparatuses; the most recent INR lab value is obtained and recorded at the time of each visit.

In one embodiment of the disclosed systems, processes, methods and apparatuses; the Warfarin dose is obtained and recorded at the time of each visit for current and future dosing.

In one embodiment of the disclosed systems, processes, methods and apparatuses; a large mixed study equation [e.g., combination of several patients' logistic equation and the use of a coefficient from this large equation] that compiles the data from several patients to accessed to obtain coefficients.

In one embodiment of the disclosed systems, processes, methods and apparatuses; any instances of bleeding episodes, estimates of blood loss and the site of bleeding is obtained and recorded at the time of each visit.

In one embodiment of the disclosed systems, processes, methods and apparatuses; any clotting events since last INR lab draw is obtained and recorded at the time of each visit.

In one embodiment of the disclosed systems, processes, methods and apparatuses; a cost effectiveness equation to choose the least expensive combination of pills in terms of dosing for each patient when dosing anticoagulants, for example, Warfarin is used at the time of each visit.

In one embodiment of the disclosed systems, processes, methods and apparatuses; the data is stored in a secure format to protect HIPAA.

In one embodiment of the disclosed systems, processes, methods and apparatuses; a velocity [i.e., change in lab value divided by time] to measure how long in minutes it would take a patient to achieve a therapeutic range on a certain dose or drug is produced at the time of each visit.

In one embodiment of the disclosed systems, processes, methods and apparatuses; a velocity to measure how long in minutes it would take a patient to be in normal INR range when stopping Warfarin is produced at the time of each visit.

In one embodiment of the disclosed systems, processes, methods and apparatuses; variables associated with supra therapeutic INR [e.g., INR >3.0] are identified at the time of each visit.

In one embodiment of the disclosed systems, processes, methods and apparatuses; variables associated with sub therapeutic INR [e.g., INR <2.0] are identified at the time of each visit.

In one embodiment of the disclosed systems, processes, methods and apparatuses; a mathematical model is used to correct for the effect on INR due to the presence of variables to adjust the Warfarin dose at the time of each visit.

In one embodiment of the disclosed systems, processes, methods and apparatuses; they can be applied to dosing of any medicine or medical treatment that requires the assessment of multiple variables.

In one embodiment of the disclosed systems, processes, methods and apparatuses; the dose will be expressed as a percent range that the patient will have a therapeutic INR with the daily dose of Warfarin.

In one embodiment of the disclosed systems, processes, methods and apparatuses; a statistical error range will be given with each dose recommendation.

In one embodiment; the disclosed systems, processes, methods and apparatuses are used to calculate the dose of insulin to achieve a therapeutic blood glucose level (e.g., <100 mg/dL).

In one embodiment; the disclosed systems, processes, methods and apparatuses are used to calculate the dose of anti-coagulant to achieve a therapeutic INR value.

In one embodiment; the disclosed systems, processes, methods and apparatuses are used to calculate the dose of Warfarin.

In one embodiment; the disclosed systems, processes, methods and apparatuses are used to calculate the dose of Coumadin, Jantoven, Marevan, Lawarin, Waran or Warfant.

In one embodiment; the disclosed systems, processes, methods and apparatuses are used to calculate the dose of heparin.

In one embodiment; the disclosed systems, processes, methods and apparatuses are used to calculate the dose for radiation treatment.

In one embodiment; the disclosed systems, processes, methods and apparatuses are used to calculate the dose of drug for chemotherapy.

In one embodiment; the disclosed systems, processes, methods and apparatuses are used to calculate the dose of depakote.

In one embodiment; the disclosed systems, processes, methods and apparatuses are used to calculate the dose of hormone therapy (e.g., Melatonin (N-acetyl-5-methoxytryptamine) [MT]; Serotonin [5-HT]; Thyroxine (or tetraiodothyronine) [T4]; Triiodothyronine [T3]; levothyroxine; Epinephrine (or adrenaline) [EPI]; Norepinephrine (or noradrenaline) [NRE]; Dopamine (or prolactin inhibiting hormone) [DPM, PIH or DA]; Antimullerian hormone (or mullerian inhibiting factor or hormone) [AMH]; Adiponectin [Acrp30]; Adrenocorticotropic hormone (or corticotropin) [ACTH]; Angiotensinogen and angiotensin [AGT]; Antidiuretic hormone (or vasopressin, arginine vasopressin) [ADH]; Atrial-natriuretic peptide (or atriopeptin) [ANP]; Calcitonin [CT]; Cholecystokinin [CCK]; Corticotropin-releasing hormone [CRH]; Erythropoietin [EPO]; Follicle-stimulating hormone [FSH]; Gastrin [GRP]; Ghrelin; Glucagon [GCG]; Gonadotropin-releasing hormone [GnRH]; Growth hormone-releasing hormone [GHRH]; Human chorionic gonadotropin [hCG]; Human placental lactogen [HPL]; Growth hormone [GH or hGH]; Inhibin; Insulin [INS]; Insulin-like growth factor (or somatomedin) [IGF]; Leptin [LEP]; Luteinizing hormone [LH]; Melanocyte stimulating hormone [MSH or α-MSH]; Orexin; Oxytocin [OXT]; Parathyroid hormone [PTH]; Prolactin [PRL]; Relaxin [RLN]; Secretin [SCT]; Somatostatin [SRIF]; Thrombopoietin [TPO]; Thyroid-stimulating hormone (or thyrotropin) [TSH]; Thyrotropin-releasing hormone [TRH]; Cortisol; Aldosterone; Testosterone; Dehydroepiandrosterone [DHEA]; Androstenedione; Dihydrotestosterone [DHT]; Estradiol [E2]; Estrone; Estriol [E3]; Progesterone; Calcitriol (1,25-dihydroxyvitamin D3); Calcidiol (25-hydroxyvitamin D3); Prostaglandins [PG]; Leukotrienes [LT]; Prostacyclin [PGI2]; Thromboxane [TXA2]; Prolactin releasing hormone [PRH]; Lipotropin [PRH]; Brain natriuretic peptide [BNP]; Neuropeptide Y [NPY]; Histamine; Endothelin; Pancreatic polypeptide; Renin; Enkephalin; and natural and synthetic analogues or drugs).

In one embodiment; the disclosed systems, processes, methods and apparatuses are used to calculate chemical reactions with multiple ingredients.

In one embodiment; the disclosed systems, processes, methods and apparatuses are used to calculate the use of inhaled gases.

In one embodiment; the disclosed systems, processes, methods and apparatuses are used to calculate the use of electrical current needed for a power system.

In one embodiment; the disclosed systems, processes, methods and apparatuses are used to calculate and predict of future events.

In one embodiment of the disclosed method identifies the variables that affect the dosing of Warfarin, corrects for their specific affects on each individual patient, generates a dosing profile for each patient and each patient has their own equation for determining the Warfarin dose and predicting the INR.

In one embodiment of the disclosed method aids the health professional in considering all the factors that may affect the INR, rather than relying on their memory to know all the drug-drug interactions and other interactions.

Currently health care professional only use the current INR value and the previous dose of Warfarin to prescribe a new dose of Warfarin for the patient. Additionally, the health care professional may consider the patient's weight and age, and occasionally kidney function is also a consideration.

In one embodiment of the disclosed method takes into account factors that are not commonly considered by health care professionals. These factors include:
1. Apply genetic factors (included at initial interview)
2. Apply fever as a factor in dosing
3. Anticipate drug-drug interactions and then correct for them mathematically with next Warfarin dose
4. Consider diet in dosing
5. Consider alcohol use and quantify amount of alcohol
6. Consider race a factor in dosing
7. Apply liver function in dosing
8. Apply "falling events" in dosing
9. Physical activity level in dosing
10. Test each factor to determine it if it is mathematically significant to effecting INR. If the factor is not mathematically significant, it is removed from the calculation to determine the Warfarin dose. For example, "Antibiotic 1" is mathematically shown to interfere with INR but "Antibiotic 2" is shown to be not mathematically significant. However, "Antibiotic 1" at ½ dose shown to be not mathematically significant in the interference with the INR but at full dose was shown to be a factor in raising/lowering INR Each variable must first be considered and only after it has been shown not to contribute to either inhibiting or stimulating the effect of Warfarin, is it excluded from the calculation of the proper dose of Warfarin to obtain a predicted INR. Each variable has to show an influence on the lab value of INR that is not due to the Warfarin dose to be able to be considered for placement in the equation.

Having described preferred embodiments of the disclosed systems, processes, methods and apparatuses, it will now become apparent to those of ordinary skill in the art that other embodiments incorporating these concepts may be used. Accordingly, it is submitted that the disclosed systems, processes, methods and apparatuses should not be limited to the described embodiments but rather should be limited only by the spirit and scope of the appended claims.

DETAILED DESCRIPTION OF THE INVENTION

Definitions

Figure 1:
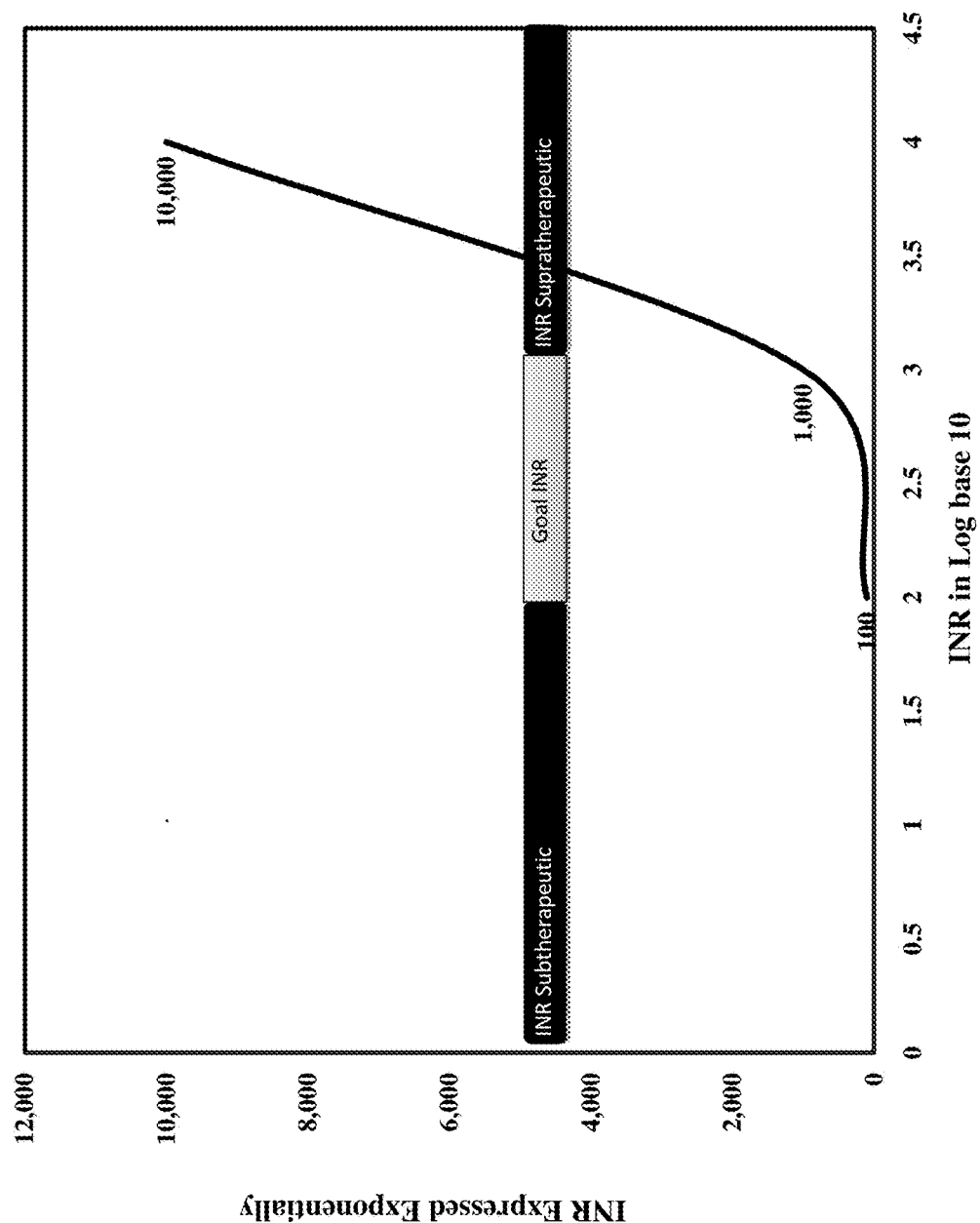
FIG. 1 illustrates a normal goal INR is 2-3. Note INR is a log base 10 scale. When expressed exponentially it is shows the large difference in INR from 2 to 4. An INR of 2 is actually 100 times while an INR of 4 is actually 10,000 times.

INR (International Normalized Ratio)—A system established by the World Health Organization (WHO) and the International Committee on Thrombosis and Hemostasis for reporting the results of blood coagulation (clotting) tests. The test uses an international sensitivity index for the specific combination of thromboplastin reagent and instrument to obtain a standardized result. Theoretically, the INR value will be the same no matter which laboratory conducts the test or which combination of thromboplastin and instrument is used for the test. International standardization allows comparison between results.

Logistic regression (also called logistic model or logit model)—A statistical test used to predict the probability of an event. The test fits the data to a logit function logistic curve. The statistical test is a linear model for binomial regression analysis using several predictor variables that can be numerical (continuous data) or categorical (discrete data).

The logistic function is powerful and robust since input values can range from negative infinity to positive infinity; however, the output is confined to values between 0 and 1.

$$Y = \frac{1}{1+e^{-z}}$$

The variable z represents the exposure to independent variables and is a measure of the total contribution of all the independent variables used in the model and is known as the logit. The variable Y represents the probability of a particular outcome.

The variable z is defined as:

$$z = \beta_o + \beta_1 x_1 + \beta_2 x_2 + \beta_3 x_3 + \ldots + \beta_n x_n$$

where $\beta_0$ is the intercept, and $\beta_1$, $\beta_2$, $\beta_3$ . . . $\beta_n$ are the regression coefficients of each independent variable $x_1$, $x_2$, $x_3$ . . . $x_n$. $\beta_0$ is the value when all independent variables are zero, that is, someone with no risk factors. Each of the regression coefficients describes the amount of that contribution to the overall risk factor. A positive regression coefficient means that the variable increases the probability, while a negative regression coefficient means that the variable decreases the probability. Additionally, a large regression coefficient means a strong influence on the probability; while a small regression coefficient means a weak influence on the probability.

Logistic regression is a way of describing interactions between continuous variables (for example age or sex) and discrete variables (for example, presence of diabetes—"yes" or "no").

An example of using a logistic regression is to determine the probability of a person having a stroke in the next 10 years from knowledge of the person's age, sex and family history.

Atrial fibrillation (AF or A-fib)—Atrial fibrillation is the most common cardiac arrhythmia (abnormal heart rhythm). It causes the heart to quiver with rapid, irregular, unsynchronized contractions. The arrhythmia involves the two upper chambers (atria) of the heart. AF can last for minutes, weeks, or years. Eventually it becomes a chronic condition with an increased risk of death. AF causes a significant increase in risk of stroke due blood pooling and forming clots in the atria. Anticoagulants, such as Warfarin, are given to patients to protect against the risk of stroke.

Algorithm—a set of rules for solving a problem in a finite number of steps.

Anticoagulation—A treatment to reduce the clotting of the blood (e.g., aspirin, heparin, Warfarin, dabigatran). The type of treatment depends on numerous issues, including cost, risk of stroke, risk of falls, compliance, and speed of desired onset of anti-coagulation.

Anticoagulant—Includes, but is not limited to Warfarin, Coumadin, Warfarin sodium salt, Warfarin derivatives, Coumadin derivatives, dicumarol, all vitamin K antagonists, all substances derived from and/or related to the foregoing substances, and any combination thereof. Anticoagulant medications directly affect coagulation reactions, thus decreasing the potential for clot formation.

Hurst Algorithm—The idea of collecting data in a binary manner with several variables for each person and analyzing the data using a mathematical technique, such as, linear or logistic regression; and then predicting the probability of an occurrence happening with a range of 0 to 1. The existence of a database and anticipation of events are key to this algorithm.

Thromboembolism—AF can cause stagnant blood to remain in the left atrium and form clots. An embolus, a blood clot in the circulatory system, occurs when a piece of a blood clot breaks off and travels in the blood circulation until it is too big to pass through the artery. This can occur in various parts of the body, depending on where the embolus ends up. The embolus blocks the artery and prevents blood from flowing further down the circulatory system. Depending on the location, size of the embolus, and the presence or absence of additional blood supply to the area, the tissue damage can be mild or lethal. An embolus lodged in an artery of the brain results in a stroke or transient ischemic attack (TIA). The formation of a thrombus, movement of the embolus, and plugging of an artery, is called a thromboembolism. The left atrial appendage is the site of thrombus formation in more than 90% of cases of thrombi associated with non-valvular atrial fibrillation.

Warfarin—It inhibits the coagulation of blood. Warfarin is used to prevent blood clots from forming or growing larger in your blood and blood vessels and is prescribed for people with irregular heartbeat, replacement or mechanical heart valves or people who have suffered a heart attack. Warfarin is also used to treat or prevent venous thrombosis and pulmonary embolism.

Warfarin is a commonly used anticoagulant and exerts its antithrombotic effects by antagonizing vitamin K metabolism. Vitamin K is an essential factor in the synthesis of many coagulations factors, including Factors II, VII, IX, X, protein C and Protein S. It is absorbed in the stomach and small intestines and is metabolized by Cytochrome P-450 system isoenzymes, which reside in the liver. Many drugs are processed by the P-450 enzyme system and their presence profoundly affects Warfarin metabolism. This, in turn, can affect the synthesis of the vitamin K dependent clotting factors.

The Vitamin K dependent clotting factors are involved in the extrinsic pathway, one of two major pathways for blood clot formation. The prothrombin time is the laboratory test used to assess the clotting activity of the extrinsic coagulation pathway. In the past, there was wide variation in the results of the test due to variability of the testing reagent, thromboplastin. To decrease this variation, the values are now normalized, with the test being expressed as an international normalized ratio (INR).

DESCRIPTION OF THE INVENTION

There is consensus regarding the optimal intensity of anticoagulation for hypercoagulable conditions. Goals for optimal INR values have been established. An INR target of 2.0 to 3.0 is recommended for the management of atrial fibrillation, pulmonary emboli, deep venous thromboses, and most hypercoagulable states (FIG. 1). For the treatment of prosthetic heart valves or failures of less intensive treatment regimens, the recommended INR target is between 2.5 and 3.5.

Figure 2:
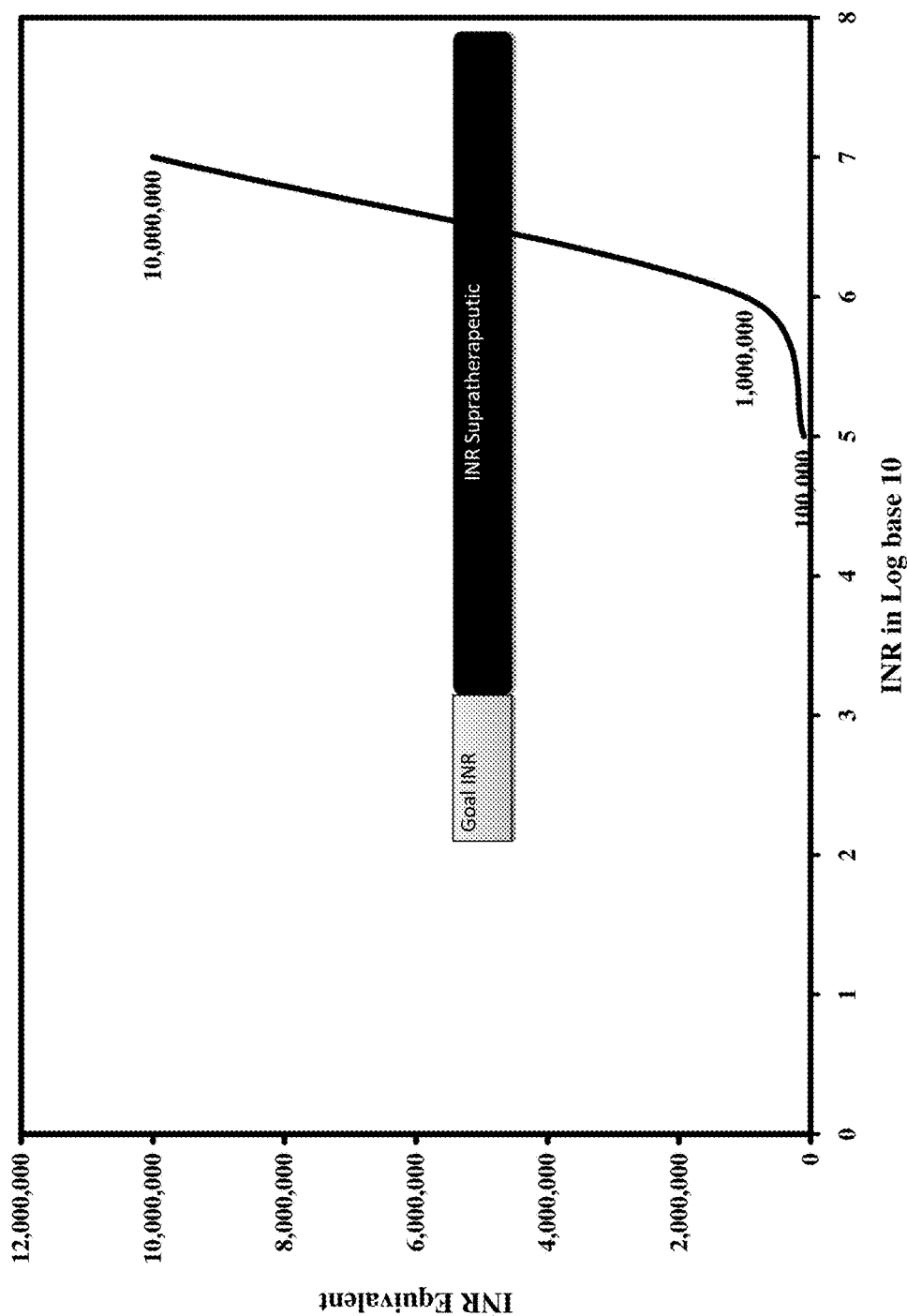
FIG. 2 shows patients with INR above 4 are at an extremely high risk of bleeding even with minor injuries.

Some studies show that up to 40% of patients who are on permanent anti-coagulation therapy do not have INR levels at their target ranges. Thrombotic events increase at an INR less than 2.0 and bleeding complications increase at an INR greater than 4.5 (FIG. 2). Multiple factors come into play, which include drug interactions, acute illnesses that either affects the liver or the kidneys, noncompliance, and management by the clinician. Experience in anticoagulation management varies widely and thus outcomes are affected.

Warfarin is usually taken once a day with or without food and the patient starts with a low dose and gradually increases or decreases the dose based on the results of blood tests. There are several risk factors that must be considered by a doctor when Warfarin is prescribed to a patient. These factors include: blood or bleeding disorder; bleeding problems; high blood pressure; heart attack; angina; heart disease; pericarditis; endocarditis; previous stroke; aneurysm; anemia; cancer; chronic diarrhea; kidney disease; liver disease; patient's age; duration of Warfarin treatment; sport activity; heredity and genetics.

Many medications and prescription drugs can interact with Warfarin, so the doctor needs to be aware of all medications the patient is taking, even if they are not known to interact. The doctor must also be aware of all nonprescription medications, vitamins, nutritional supplements and herbal products being taken or planned to be taken by the patient. Especially of note are antibiotics; aspirin or aspirin-containing products; nonsteroidal anti-inflammatory drugs; ibuprofen; naproxen; heparin; medications for cancer, cholesterol, colds, allergies, depression, diabetes, digestive problems, gout, heart disease, mental illness, pain, seizures, thyroid problems and tuberculosis; oral contraceptives; streptokinase; ticlopidine; and urokinase.

Herbal and botanical products also can be of concern since they are not regulated by the FDA and can contain wildly varying concentrations of unknown chemicals. Some of these products are Bromelains, Chamomile (*Matricaria recutita*), Coenzyme $Q_{10}$, Cranberry products, Danshen, Dong quai, Echinacea (*Echinacea purpurea* and *Echinacea* spp.), Evening Primrose (*Oenothera biennis*), Feverfew (*Tanacetum parthenium*), Garlic (*Allium sativum*), Ginger (*Zingiber officinale*), Ginkgo (*Ginkgo biloba*), Ginseng (*Panax* spp.), Goldenseal (*Hydrastis canadensis*), Kava Kava (*Piper methysticum*), Milk Thistle (*Silybum mari-*

*anum*), Saw Palmetto (*Serenoa repens*), St. John's Wort (*Hypericum perforatum*), and Valerian (*Valeriana officinalis*).

Additionally, the doctor should know if the patient has thyroid problems, diabetes, infections, gastrointestinal problems and diarrhea; or is pregnant, breast-feeding, a heavy alcohol drinker, pending surgery or immunizations.

The doctor must know about symptoms indicating an excess of Warfarin. These symptoms can include: headache, dizziness, weakness, pain, swelling or discomfort; unusual bleeding from a cut, nose or gums; coughing up or vomiting blood; unusual bruising; increased menstrual or vaginal bleeding; dark urine and tarry black bowel movements.

The doctor also must know if the patient has any critical symptoms: including hives; rash; itching; difficulty breathing or swallowing; swelling; chest pain; yellowing of the skin or eyes; flu-like symptoms; numbness, tingling, pricking, or burning. Additionally, Warfarin can cause necrosis, gangrene, and ulcers.

EXAMPLES

Example 1

A patient is referred to a physician to receive treatment with a blood anticoagulant. The physician identifies the patient as requiring long term anticoagulation treatment with Warfarin and needs specialized dosing for the treatment based on several variables. The patient is first enrolled in the database.

Figure 3:
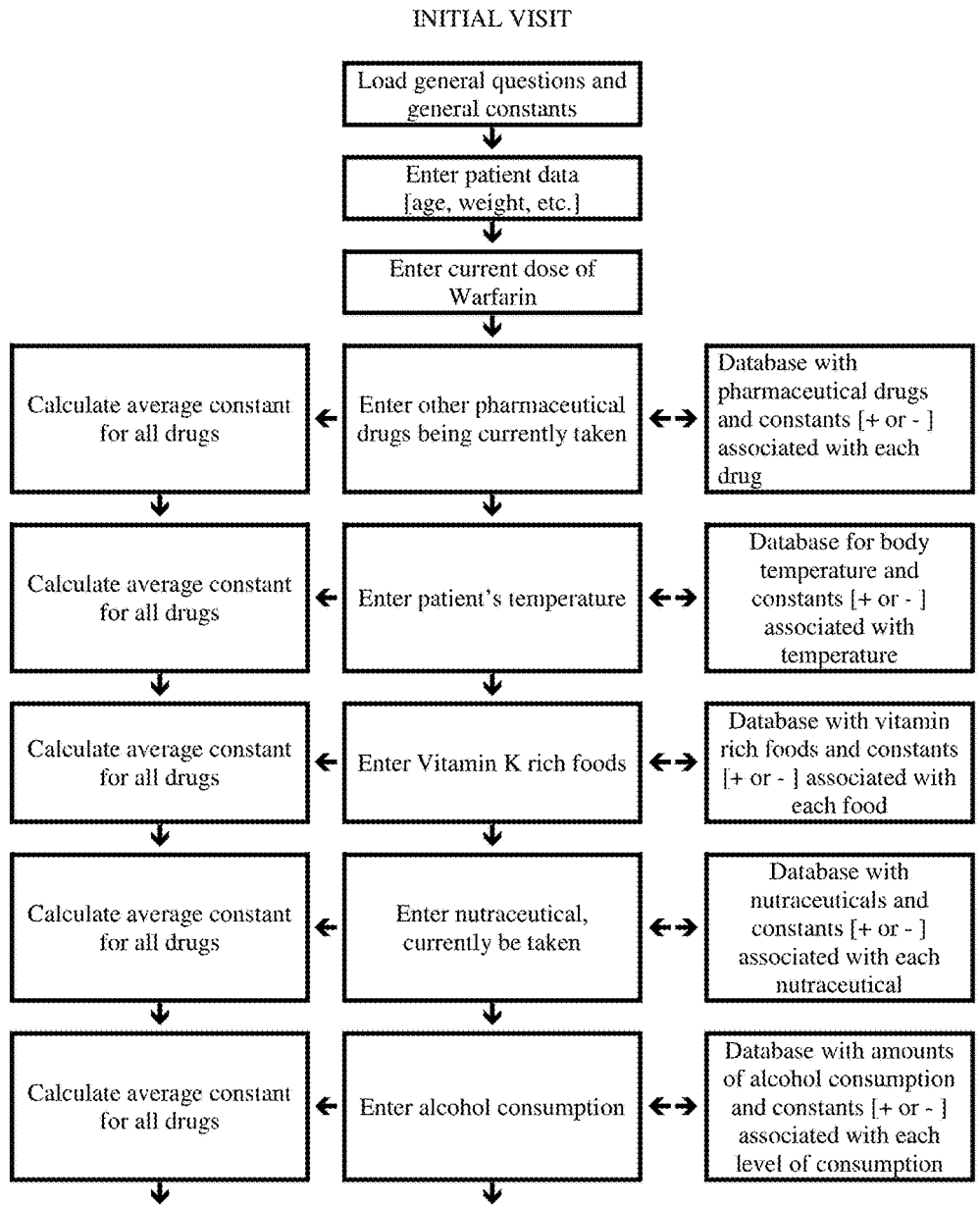
FIG. 3 shows a questionnaire and intake procedure for a patient's initial visit to a health care provider.
Figure 3:
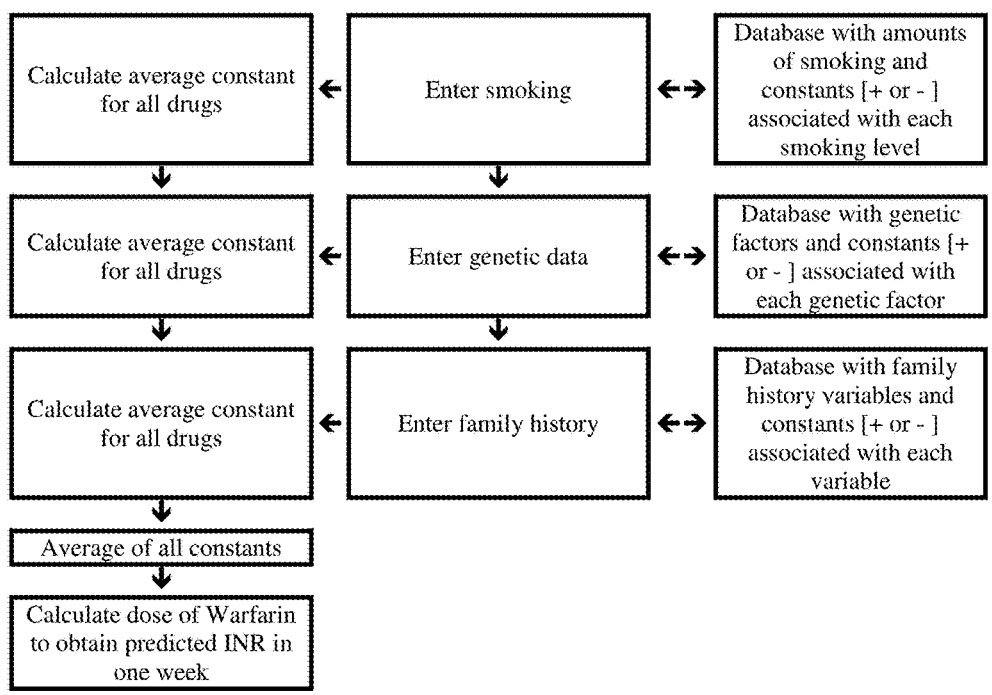

The system presents a series of questions to be asked by the physician and displays lists of possible answers or choices for each question. The physician collects the initial data including ethnicity, gender, reason for anticoagulation (disease state), age, time needed for anti-coagulation treatment (lifetime 6 months), goal International Normalized Ratio (INR) 2-3 or 2.5-3.5, and initial set of liver enzymes lab values (FIG. 3). Additional information includes a patient's genetic factors, diet, drug interactions, illness, and/or compliance with recommended dosing schedules, or any other information that may affect a patient's response to anticoagulant therapy (Table 2).

TABLE 2

| Initial Data at First Patient Encounter |
|---|
| Age in years |
| Gender |
| Women menopause status |
| Ethnic background |
| Indications/Indications for Warfarin |
| Lifelong need for Warfarin or short term use |
| Goal INR |
| Initial Liver Enzymes value |
| Kidney Function |
| Genetic Information |
| Y Factor INR lab value |

The physician draws blood for a lab test to determine the INR. This value is recorded into the system.

The physician follows the series of question presented by the system (Table 3). The physician discusses the current medications being taken by the patient. Medications that are listed by the system are recorded: dose, route of administration, and number of days on medication.

TABLE 3

| |
|---|
| X1 Average daily Warfarin dose in mg |
| X2 Diuretic |
| X3 Antibiotic |
| X4 Amiodarone |
| X5 Multi-Vitamin |
| X6 Selective Serotonin Re-Uptake Inhibitors (SSRI) |
| X7 Thyroid Hormone replacement |
| X8 Nonsteroidal Anti-Inflammatory Drug (NSAID), Lovenox, Aspirin (ASA) |
| X9 Antiepileptic drug |
| X10 Antifungal |
| X11 Proton Pump Inhibitor |
| X12 Herbals Medications |
| X13 Fever |
| X14 Diarrhea |
| X15 Compliance |
| X16 Recent Fall |
| X17 Change in diet with regard to vitamin K food |
| X18 Weight in kilograms |
| X19 Number of cigarettes smoked per day |
| X20 Number of alcoholic drinks since last lab |

The physician enters the current weight of the patient into the system and asks about changes in diet, especially vitamin K containing food, such as spinach or any green leafy vegetable. Any vitamin K rich foods are recorded into the system and a value is recorded for their quantity.

The physician asks about herbal medications, and any herbal medications are recorded into the system and a value is recorded for their quantity.

The physician asks about alcohol consumption and average number of drinks a day, and records into the system a value for the quantity.

The physician asks about smoking and records number of cigarettes, and records into the system a value for the quantity.

The physician asks if the patient has diarrhea or loose stools, and records into the system a value for the frequency.

The physician asks the patient if they have a fever, and records into the system a value for the severity, duration and frequency.

The physician asks the patient if they have fallen recently, and records into the system a value the severity and frequency.

The physician asks the patient about their compliancy with Warfarin, and records into the system a value for the percentage.

The physician analyzes the most recent liver enzymes lab tests and records the values.

The physician asks about bleeding episodes and records into the system if the patient has bleed, from where and how much.

The system calculates a dose of Warfarin and gives a value for the percent probability of achieving a therapeutic INR at the next visit.

The physician gives the patient a new dose and schedules new lab tests for the next visit.

Figure 4:
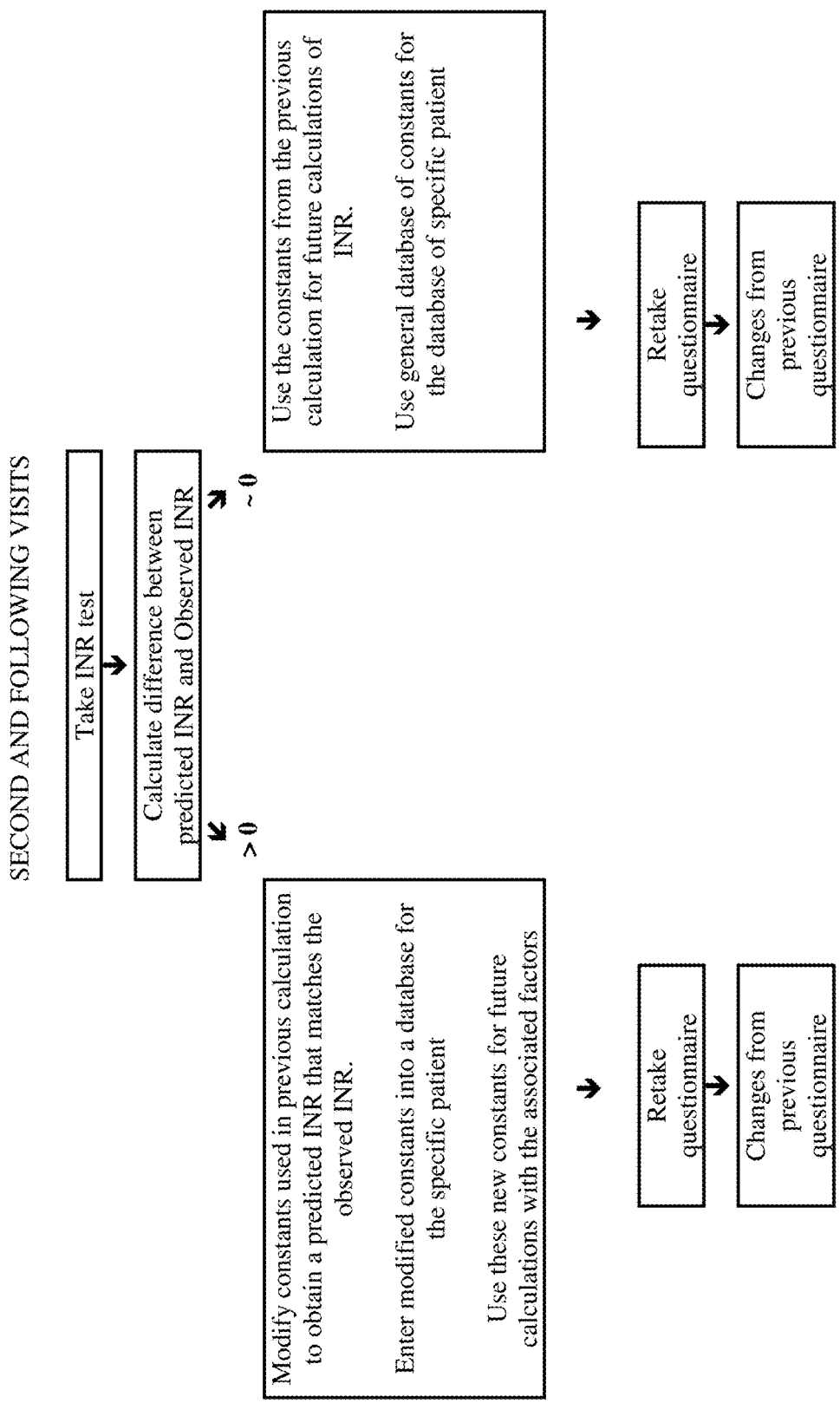
FIG. 4 shows a questionnaire and intake procedure for a patient's second and following visits to a health care provider.
Figure 4:
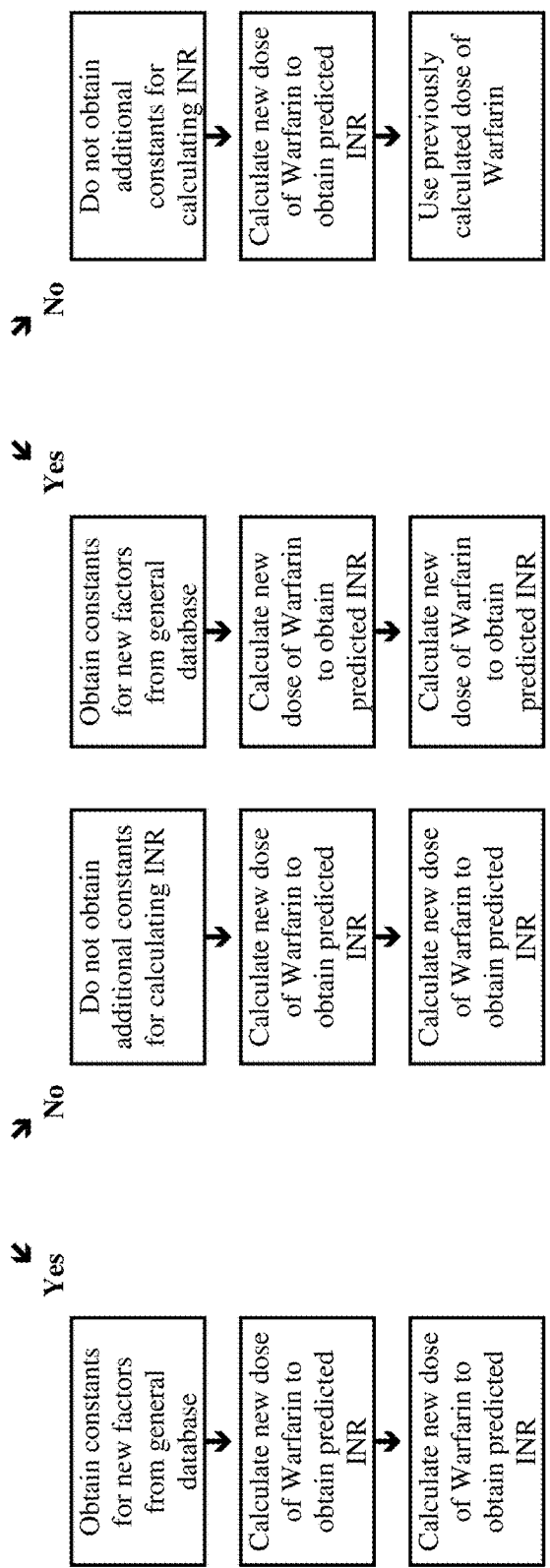

The health care provider repeats the intake and questionnaire to determine if any of the information has changed from the previous visit (FIG. 4).

Example 2

Patient 1

A 70 year old white man with a history of blood clots in the lungs and arm due to atrial fibrillation has high blood pressure and frequently gets skin infections. Through analysis of his past visits these are the variables that contribute to his INR (Table 4).

TABLE 4

| Significant Variables | Corrective Coefficients |
|---|---|
| Antibiotic Doxycycline 100 mg | +1.5 |
| Diuretic Lasix 80 mg every 24 hours | +1.0 |
| Diarrhea | +0.5 |
| Intake vitamin K foods >3 servings | −0.75 |
| Missing dose of Warfarin 1 day | −0.025 |
| Aspirin 325 mg every 8 hours | −0.10 |

Patient 2

A 32 year old woman with factor V Leiden, which is a disorder that predisposes her to clots. She enjoys wine tasting and drinks socially. She recently lost weight. She sometimes gets migraine headaches and uses Tylenol. Through analysis of her past visits these are the variables that contribute to her INR (Table 5).

TABLE 5

| Significant Variables | Corrective Coefficients |
|---|---|
| Alcohol >3 drinks | +2.0 |
| Weight 5 kg weight loss | −1.0 |
| Tylenol 650 mg | +0.75 |

Example 3

A simulation of the software and mathematical model is disclosed.

During each patient's visit, the doctor records any changes in the parameters used in the model. Table 6 shows how the data from an initial clinic visit is stored in a database, as 1 for yes and 0 for no.

TABLE 6

| | |
|---|---|
| Age 30-40 | 0 |
| age 40-50 | 0 |
| Age 50-60 | 0 |
| Age 60-70 | 1 |
| Age 70-80 | 0 |
| Age 80-90 | 0 |
| Age 90+ | 0 |
| Man | 0 |
| Woman | 1 |
| Menopause | 1 |
| White | 1 |
| Black | 0 |
| Asian | 0 |
| Atrial fibrillation | 1 |
| Pulmonary embolism | 0 |
| Heart valve | 0 |
| Factor V Leiden | 0 |
| INR goal 2-3 | 1 |
| INR 2.5 to 3.5 | 0 |
| Liver Function normal | 1 |
| Kidney function normal | 1 |
| Genetic information | 0 |

After 4 visits this patient has a personal equation and trends can be taken from that equation (Table 7). For example, if she plans on drinking wine again or needs to be on an antibiotic the computer can adjust her Warfarin to keep it in range 2-3 by logistic regression.

TABLE 7

| | visit 1 | visit 2 | visit 3 | visit 4 |
|---|---|---|---|---|
| Y INR 1-2 | 0 | 0 | 0 | 0 |
| Y INR 2-3 | 0 | 1 | 0 | 1 |
| Y INR 3-4 | 1 | 0 | 0 | 0 |
| Y INR 4-5 | 0 | 0 | 1 | 0 |
| Y INR 5-6 | 0 | 0 | 0 | 0 |
| Y INR >6 | 0 | 0 | 0 | 0 |
| X1 Warfarin 5 mg | 0 | 1 | 1 | 1 |
| X1 Warfarin 6 mg | 0 | 0 | 0 | 0 |
| X1 Warfarin 7 mg | 1 | 0 | 0 | 0 |
| X1 Warfarin 8 mg | 0 | 0 | 0 | 0 |
| X1 Warfarin 9 mg | 0 | 0 | 0 | 0 |
| X1 Warfarin 10 mg | 0 | 0 | 0 | 0 |
| X2 Diuretic hydrochlorothiazide (HCTZ) 25 mg every 24 hrs | 1 | 1 | 0 | 0 |
| X2 Lasix 40 mg | 0 | 0 | 1 | |
| X2 Lasix 60 mg | 0 | 0 | 0 | 1 |
| X2 Lasix 80 mg | 0 | 0 | 0 | 0 |
| X2 Lasix 160 mg | 0 | 0 | 0 | 0 |
| X3 Antibiotic Tetracycline Doxycycline 100 mg by mouth twice a day | 1 | 0 | 0 | 0 |
| X3 Antibiotic Macrolide | 0 | 0 | 0 | 0 |
| X3 Penicillin Based | 0 | 0 | 0 | 0 |
| X3 Cephalosporin | 0 | 0 | 0 | 0 |
| X3 Antibiotic flurouquin | 0 | 0 | 0 | 0 |
| X4 Amiodorane | 0 | 0 | 0 | 0 |
| X5 Vitamin | 0 | 0 | 0 | 0 |
| X6 Selective Serotonin Re-Uptake Inhibitors (SSRI) | 0 | 0 | 0 | 1 |
| X7 Thyroid replacement | 0 | 0 | 0 | 0 |
| X8 Nonsteroidal Anti-Inflammatory Drug (NSAID), Lovenox, Aspirin (ASA) | 1 | 0 | 0 | 0 |
| X9 Antiepileptic | 0 | 0 | 0 | 0 |
| X10 Antifungal | 0 | 0 | 0 | 0 |
| X11 Proton Pump Inhibitor | 0 | 0 | 0 | 0 |
| X12 Herbal medicines | 0 | 0 | 0 | 0 |
| X13 Fever | 1 | 0 | 0 | 0 |
| X14 Diarrhea | 0 | 0 | 0 | 0 |
| X15 Noncompliance | 0 | 0 | 0 | 0 |
| X16 Recent fall | 0 | 0 | 0 | 0 |
| X17 Diet change | 0 | 0 | 0 | 0 |
| X18 Weight in Kilo 70 kg | 0 | 0 | 0 | 1 |
| X18 Weight in Kg 80 kg | 1 | 1 | 1 | 0 |
| X18 Weight in kg 90 kg | 0 | 0 | 0 | 0 |
| X18 Weight in kg 100 kg | 0 | 0 | 0 | 0 |
| X18 Weight in kg 120 kg | 0 | 0 | 0 | 0 |
| X18 Weight in kg 150 kg | 0 | 0 | 0 | 0 |
| X19 Number of cigarettes <10 | 0 | 0 | 0 | 0 |
| X19 Number of cigarettes >10 | 0 | 0 | 0 | 0 |
| X20 Number of alcohol drinks, 3 per day | 0 | 0 | 0 | 0 |
| X20 Alcoholic drinks >3 per day | 0 | 0 | 1 | 0 |

Example 4

First Visit to a Health Care Provider for Initiation of Warfarin Use

The patient is a 65 year old white woman visiting a health care provider for her first dose of Warfarin. She is postmenopausal, her diagnosis for Warfarin is atrial fibrillation, and she will need lifelong therapy of Warfarin to avoid formation of blood clots. The goal INR is 2-3. Her liver and kidney functions are within normal limits. She knows no genetic information. She is given a dose of 7 mg of Warfarin by mouth everyday and told to return to the office in 1 week. She is advised to call the office if she has bleeding gums, bloody noses or easy bruising. Also, warned about binge alcohol drinking which can cause bleeding or eating foods with vitamin K [green vegetables, such as, spinach] which can cause clots.

Visit 2

The 65 year old woman returns to the office in 1 week and her INR is 3.4, but she had no bleeding and, upon physical exam, no signs of bleeding. Going over the patient's current medications she is on hydrochlorothiazide (HCTZ) 25 mg by mouth each day for high blood pressure, an antibiotic Doxycycline 100 mg by mouth every 12 hours for a skin infection, and she took some aspirin for a headache. She smoked no cigarettes, no alcohol, no falls, no diet of vitamin K foods, weighs 82 kilograms and takes all medicine as directed. She is given a reduced dose of 5 mg of Warfarin a day. She returns in 2 weeks.

Visit 3

The patient returns after reducing her Warfarin dose to 5 mg by mouth every day. Her INR is now on target at 2.5. She now only takes HCTZ 25 mg every day. There is no alcohol, cigarettes, fevers, bleeding episodes, diarrhea, falls, and she is compliant. She is to remain on same dose of Warfarin and to return in 1 month for another INR reading.

Visit 4

In 1 month, the patient returns and her INR is 4.3. She has stopped HCTZ and now takes Lasix, a stronger drug for high blood pressure, 40 mg by mouth every 24 hours. She admits to wine tasting last evening and having well over 3 glasses of wine. She has no bleeding events, and weight is the same 82 kg, no fevers, no diarrhea, no falls. Patient told to hold medicine for one day and not to use alcohol. Patient then advised to restart Warfarin at 5 mg and return in 2 weeks.

Visit 5

The patient returns in 2 weeks and her INR is at goal 2.3. Her Lasix was increased from 40 mg a day to 60 mg a day and she has lost weight. She now weighs 73 kg. She was started on an antidepressant due to stress from family issues. No alcohol, no cigarettes, no diarrhea, no falls, no change in diet and she takes medicine as prescribed by her doctor. She will return in for monthly as long as her INR remains on goal and she has not adverse reactions.

Example 5

A health care provider has a patient on Warfarin. The nurse takes their INR lab value and enters it into a software program. The health care provider has the software open on a computer or a hand held device. Then the provider asks the patient the relevant questions, does a physical exam and inputs this into the electronic form. After the data is collected and analyzed, then a recommended dose for the patient is given with a percent range that the patient will have therapeutic INR with this daily dose of Warfarin.

For example, the software may have a readout of "Given the data collected the dose of 5 mg by mouth every 24 hours of Warfarin will result in an INR of between 2-3 with a 70%-90% possibility if compliant with medications and no other variables change."

Example 6

A diabetes patient tells the health care provider their average daily blood glucose value. A health care provider can do this over a phone or via the Internet. A physical exam, review of biological systems, and medicine reconciliation is done and the information is put into software program. Then, for example, the software may have readout of "Given the data collected, the dose of 100 units of insulin Subcutaneous every 24 hrs will result in blood glucose of between 90-150 with a 50%-90% possibility if compliant with medications and no other variables change."

Example 7

A patient goes to a physician with a diagnosis of atrial fibrillation needing anti-coagulant therapy. The physician takes a complete medical history, including questions concerning current drug prescriptions, typical foods, use of herbal medicines, intake of alcohol (amount, frequency and type), estimated percent compliance of previous prescribed anticoagulant therapy, episodes of bleeding, ethnicity, genetic information, measurement of kidney function, measurement of liver function, number of episodes of diarrhea, episodes of falling, number of instances of fevers, tobacco use (type, quantity), site of bleeding.

The patient is a 55 year-old male eating a typical Western diet, drinking a glass of wine 2 days a week, no history of tobacco use, normal kidney and liver function; however takes 30 mg of Lasix per day. The INR goal for the patient is "3".

Answers to the physician's questions are entered into software program to generate a suggested dose of anticoagulate.

The physician prescribes Warfarin to the patient with the suggested dose from the software program. The patient is told to return in one week. The patient takes an INR test before the next visit.

The physician repeats the medical history intake with questions seeking any changes from the previous week. Any changes are entered in the patient's data file. The current INR is entered in the software program. The patient's equation to determine the dose of Warfarin is recalculated taking into account changes to the medical history and differences between the predicted INR and observed INR.

The physician prescribes the new dose of Warfarin suggested by the equation. The patient is again told to return in one week and to take an INR test before the next visit.

Figure 5:
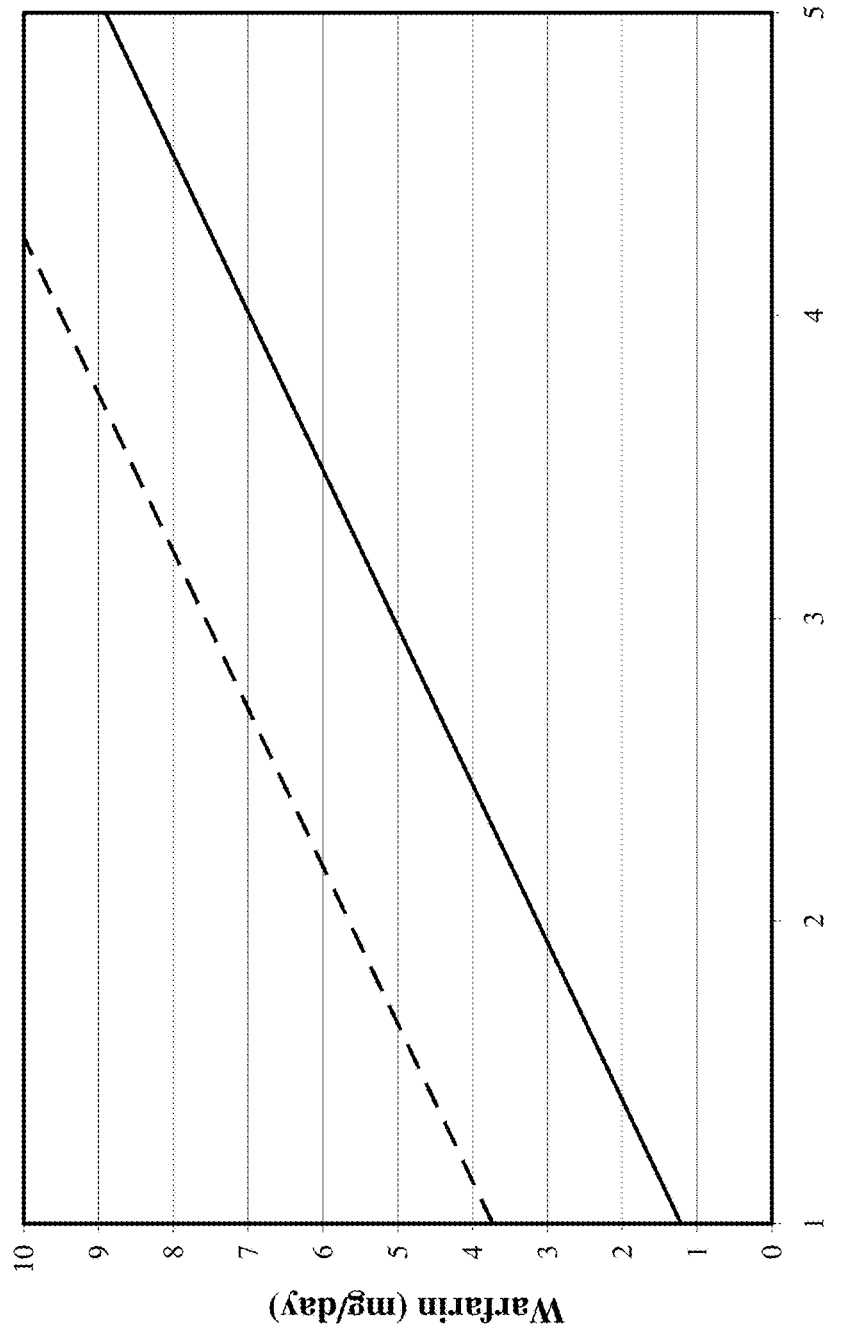
FIG. 5 shows regression lines generated by the logistic model for the individual. The dotted lines show the relationship between Warfarin and INR after 20 visits to the health care provider. The solid line shows the relationship between Warfarin and INR for the patient after his prescription of Lasix is increased from 30 mg/day to 60 mg/day. The interaction with Warfarin is additive, which gives parallel lines.

After 20 visits, the equation for estimating the patient's Warfarin dose has a confidence of 95% and is calculated as (FIG. 5):

$$y(INR)=0.52(\text{Warfarin in mg})-0.9393$$

to produce an INR of 3, the Warfarin dose [X] is:

$$3=0.52 [X]-0.9393$$

$$3.9393=0.52 [X]$$

$$3.9393/0.52=[X]$$

$$7.58 \text{ mg}=X$$

$$7.5 \text{ mg/day}$$

Therefore, the equation for this patient has a slope of 0.52 with an x-intercept of −0.9393. This formula is able to suggest a dose that enables the patient to maintain his INR at 3.

Later on, the patient's dose of Lasix is increased to 60 mg/day. The increased dose of Lasix causes the INR formula to suggest a dose that is too high and produces an observed INR of 4-5.

Over the next weekly visits the INR formula is modified to (FIG. 5):

$$y(INR)=0.52(\text{Warfarin in mg})+0.37$$

to produce an INR of 3, the Warfarin dose [X] is:

$$3=0.52 [X]+0.37$$

$$2.63=0.52 [X]$$

$$2.63/0.52=[X]$$

$$5.05 \text{ mg}=X$$

$$5 \text{ mg/day}$$

Therefore, if the patient is taking 60 mg/day of Lasix, the slope of the equation remains the same at 0.52; however, the x-intercept is shifted to +0.37. This means that a patient, who increases Lasix from 30 mg/day to 60 mg/day, causes the equation to have an additional correction factor of 1.31. This value can be used as a starting point for correcting the INR equation for other patients who increase their Lasix.

Example 8

The patient in Example 7 returns to taking Lasix 30 mg/day and Warfarin 7.5 mg/day, and he maintains an INR of ~3. He remains compliant with regular intake of the proper dosage and regular laboratory testing of his INR.

He develops a minor infection and is prescribed amoxicillin 500 mg and clavulanate 250 mg to be taken 3 times a day for 7 days. Additionally the patient is prescribed loratadine 10 mg/day for 4 days, gabapentin 300 mg/day, and oxycodone/acetaminophen 7.5/500 mg (2 pills every 6 hours).

The patient's INR is 3 before taking the prescribe antibiotics. The physician maintains the Warfarin dose of 7.5 mg and has the patient return in 1 week for an INR test. At the next visit, the patient reported a few episodes of loose bowels and his INR is 2.5.

During his next office visit to check his INR, it is determined that his INR is 6. A test a week later indicates the INR is 9. Warfarin intake was immediately stopped and emergency procedures of a blood transfusion and a dose of Vitamin K are able to return the INR to 3.5.

The above data was entered into the patient's INR program and a new formula was generated to predict a Warfarin dose when the patient is prescribed amoxicillin (500 mg, 3 times per day).

The equation before the prescription of amoxicillin was:

$y(INR)=0.52(Warfarin\ in\ mg)-0.9393$

Figure 6:
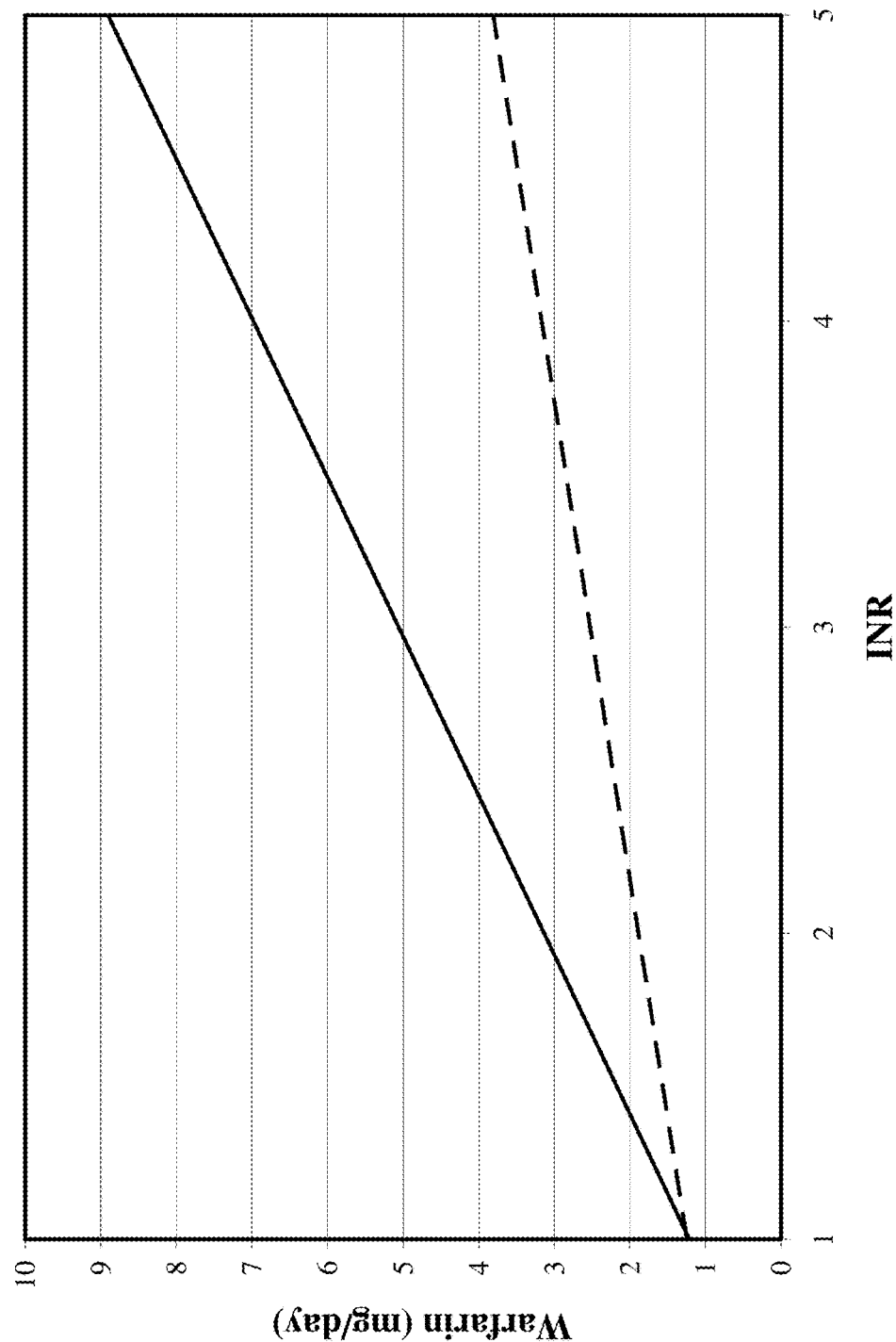
FIG. 6 shows regression lines generated by the logistic model for the individual. The solid line shows the relationship between Warfarin and INR for the patient with a prescription of Lasix 60 mg/day. The dotted line shows the relationship between Warfarin and INR for the patient after taking a prescription of antibiotic. The interaction with Warfarin is synergistic or multiplicative, which gives lines that meet at the y-intercept and are not parallel.

However, after being prescribed amoxicillin, the equation is (FIG. 6):

$y(INR)=1.56(Warfarin\ in\ mg)-0.9393$ to produce an INR of 3, the Warfarin dose [X] is:

$3=1.56\ [X]-0.9393$ $3.9393=1.56\ [X]$ $3.9393/1.56=[X]$ $2.52\ mg=X$ $2.5\ mg/day$ Therefore, in the future when the patient is prescribed amoxicillin, the patient's program will automatically correct for the increase activity of Warfarin due to the interaction with amoxicillin and reduce the dose by ⅓.

Example 9

Y. H. Chan shows how logistic regression can be used to predict the probability of an individual having a systolic blood pressure ≥180 [Chan, Y. H., 2004, Basic Statistics For Doctors, Singapore Med. J., Vol 45(4): 149-153 and Chan Y. H., 2004, Biostatistics 201: Linear regression analysis, Singapore Med. J., Vol 45, 55-61]. Similar analyses can be used in the disclosed methods for anticoagulant therapy and long-term therapy.

To model for the predictors of systolic blood pressure (SBP) ≥180 mmHg, a categorical dichotomous outcome (Table 8), the appropriate multivariate analysis is a logistic regression.

TABLE 8

Frequency distribution of SBP ≥180 mmHg

| | | Frequency | Percent | Valid percent | Cumulative percent |
|---|---|---|---|---|---|
| Valid | No | 40 | 72.7 | 72.7 | 72.7 |
| | Yes | 15 | 27.3 | 27.3 | 100.0 |
| | Total | 55 | 100.0 | 100.0 | |

In order to determine the predictors for SBP ≥180 mmHg, the numerical coding for SBP ≥180 mmHg must be "bigger" than that of SBP <180 mmHg, for example "1" & "0", respectively. A typical computer program to conduct a logistic regression is SPSS (Statistical Package for the Social Sciences), which uses the "higher coded" category to be the predicted outcome.

Since smoker and race are categorical, a reference group is needed (the default in SPSS is the "highest coded"). For race, Chinese is usually selected to be the reference and the standard coding is 1=Chinese, 2=Indian, 3=Malay, 4=Others.

Additionally, the reference category smoking is changed to coding of 1=smoker and 0=non smoker. The output should be selected for "easy interpretation"; that is, comparing the smoker with the non-smoker of having SBP ≥180. Tables 9-13 show the output generated by SPSS when a logistic regression is performed.

TABLE 9

Number of cases in model
Case processing summary

| Unweighted Case[a] | | N | Percent |
|---|---|---|---|
| Selected cases | Included in analysis | 55 | 100.0 |
| | Missing cases | 0 | 0.0 |
| | Total | 55 | 100.0 |
| Unselected Cases | | 0 | 0.0 |
| Total | | 55 | 100.0 |

[a]If weight is in effect, the classification table should be checked for the total number of cases.

55 cases were included in the analysis. A subject will be omitted from the analysis if any one of the data points (for example, age) is missing, regardless of the availability of the others.

TABLE 10

Predicted outcome coding
Dependent variable encoding

| Original value | Internal value |
|---|---|
| No | 0 |
| Yes | 1 |

Table 10 is very important because it shows which category SPSS is using as the predicted outcome, the higher coded category (having SBP ≥180 mmHg).

TABLE 11

Amount of variation explained by the model.

| Step | −2 Log likelihood | Cox & Snell R Square | Nagelkerke R Square |
|---|---|---|---|
| 1 | 40.819 | 0.349 | 0.506 |

The Nagelkerke R Square shows that about 50% of the variation in the outcome variable (SBP ≥180) is explained by this logistic model (Table 11).

TABLE 12

Estimates of the logistic regression model
Variables in the equation

| | | B | S.E. | WALD | df | SIG. | EXP(B) | 95.0% C.I. for EXP(B) Lower | 95.0% C.I. for EXP(B) Upper |
|---|---|---|---|---|---|---|---|---|---|
| Step 1[a] | AGE | 0.209 | 0.063 | 11.007 | 1 | .001 | 1.233 | 1.089 | 1.395 |
| | SMOKER(1) | 2.292 | 0.986 | 5.401 | 1 | .020 | 9.896 | 1.432 | 68.380 |
| | RACE | | | 1.627 | 3 | .653 | | | |
| | RACE(1) | 0.640 | 1.009 | 0.402 | 1 | .526 | 1.896 | 0.263 | 13.696 |
| | RACE(2) | 1.303 | 1.136 | 1.316 | 1 | .251 | 3.681 | 0.397 | 34.101 |
| | RACE(3) | −0.097 | 1.230 | 0.006 | 1 | .937 | 0.908 | 0.081 | 10.113 |
| | constant | −14.462 | 4.005 | 13.041 | 1 | .000 | 0.000 | | |

Chinese is the reference category for Race. In Table 12, Race(1) refers to comparing the Indian with Chinese; Race(2) refers to comparing the Malay with Chinese and Race(3) for Others comparing with Chinese.

The results in Table 12 are interpreted by looking at the Wald estimates, which give the "importance" of the contribution of each variable in the model. The higher the value, the more "important" it is.

A predictor-model would be interested in both age and smoking status as important risk factors to having SBP ≥180, with p-values of 0.001 and 0.020 (given by the Sig column), respectively. The Exp(B) gives the Odds Ratios. Since age is a quantitative numerical variable, an increase in one-year in age has a 23.3% (95% CI 8.9% to 39.5%) increase in odds of having SBP ≥180. The value of 23.3% is obtained by taking Exp(B) for age −1.

SMOKER(1) in Table 12 is shown by the coding for the categorical variables Table 13. The reference group for a particular variable is given by the row of zeros. Thus for Smoker, the reference group is the non-smoker. A smoker compared to a non-smoker is 9.9 (95% CI 1.4 to 68.4) times more likely to have SBP ≥180.

TABLE 13

Categorical variables coding

| | | FREQUENCY | Parameter coding (1) | Parameter coding (2) | Parameter coding (3) |
|---|---|---|---|---|---|
| RACE | CHINESE | 23 | 0.000 | 0.000 | 0.000 |
| | INDIAN | 13 | 1.000 | 0.000 | 0.000 |

TABLE 13-continued

Categorical variables coding

| | | FREQUENCY | Parameter coding (1) | Parameter coding (2) | Parameter coding (3) |
|---|---|---|---|---|---|
| | MALAY | 10 | 0.000 | 1.000 | 0.000 |
| | OTHERS | 9 | 0.000 | 0.000 | 1.000 |
| SMOKER | NO | 23 | | | |
| | YES | 32 | | | |

TABLE 14

An 8-variable logistic model with multicolinearity
Variables in the Equation

| | | B | S.E. | WALD | df | Sig. |
|---|---|---|---|---|---|---|
| Step 1 | V1 | −1062.640 | 56906.272 | .000 | 1 | .985 |
| | V2 | −2033.243 | 107665.309 | .000 | 1 | .985 |
| | V3 | −2282.536 | 121116.943 | .000 | 1 | .985 |
| | V4 | −462.334 | 26296.043 | .000 | 1 | .986 |
| | V5 | 1000.935 | 53615.449 | .000 | 1 | .985 |
| | V6 | 65.543 | 5358.046 | .000 | 1 | .990 |
| | V7 | 764.889 | 40207.609 | .000 | 1 | .985 |
| | V8 | −62.261 | 4286.793 | .000 | 1 | .988 |
| | constant | −829.405 | 44003.539 | .000 | 1 | .985 |

TABLE 15

Correlation matrix of the 8-variable model

| | | Constant | V1 | V2 | V3 | V4 | V5 | V6 | V7 | V8 |
|---|---|---|---|---|---|---|---|---|---|---|
| Step 1 | Constant | 1.000 | −0.878 | −0.892 | 0.965 | −0.920 | −0.924 | −0.917 | −0.523 | −0.412 |
| | V1 | −0.878 | 1.000 | 0.659 | −0.831 | 0.743 | 0.938 | 0.766 | 0.144 | 0.389 |

TABLE 15-continued

Correlation matrix of the 8-variable model

|  | Constant | V1 | V2 | V3 | V4 | V5 | V6 | V7 | V8 |
|---|---|---|---|---|---|---|---|---|---|
| V2 | −0.892 | 0.659 | 1.000 | −0.887 | 0.866 | 0.746 | 0.809 | 0.679 | 0.222 |
| V3 | 0.965 | −0.831 | −0.887 | 1.000 | −0.980 | −0.917 | −0.887 | −0.555 | −0.374 |
| V4 | −0.920 | 0.743 | 0.866 | −0.980 | 1.000 | 0.877 | 0.832 | 0.598 | 0.342 |
| V5 | −0.924 | 0.938 | 0.746 | −0.917 | 0.877 | 1.000 | 0.799 | 0.280 | 0.378 |
| V6 | −0.917 | 0.766 | 0.809 | −0.887 | 0.832 | 0.799 | 1.000 | 0.620 | 0.150 |
| V7 | −0.523 | 0.144 | 0.679 | −0.555 | 0.598 | 0.280 | 0.620 | 1.000 | −0.155 |
| V8 | −0.412 | 0.389 | 0.222 | −0.374 | 0.342 | 0.378 | 0.150 | −0.155 | 1.000 |

Table 14 shows an 8-variable model with the correlation matrix between any two variables given in Table 15.

TABLE 16

Correlation matrix for SBP model

|  |  | Constant | SMOKER(1) | RACE(1) | RACES(2) | RACES(3) | AGE |
|---|---|---|---|---|---|---|---|
| Step 1 | Constant | 1.000 | 0.345 | −0.326 | −0.265 | −0.415 | −0.953 |
|  | SMOKER(1) | 0.345 | 1.000 | 0.073 | 0.081 | −0.122 | −0.450 |
|  | RACE(1) | −0.326 | 0.073 | 1.000 | 0.700 | 0.652 | 0.068 |
|  | RACE(2) | −0.265 | 0.081 | 0.700 | 1.000 | 0.585 | 0.030 |
|  | RACE(3) | −0.415 | −0.122 | 0.652 | 0.585 | 1.000 | 0.215 |
|  | AGE | −0.953 | −0.450 | 0.068 | 0.030 | 0.215 | 1.000 |

Table 16 shows the correlations between any two variables. It is expected to be moderate to high correlations within Race; the correlation values among age, smoker and race are low. The correlation between age and the constant is rather high (r=−0.953) which shows some multicolinearity.

In the correlation matrix, it is not easy to determine the location of the multicolinearity. Also, another drawback with the correlation matrix is that multicolinearity will not be shown between one variable with a combination of variables.

A simple but sometimes subjective technique is to inspect the magnitude of the standard error (SE) of each variable. The SEs in Table 14 are very large, which imply multicolinearity exists and the model is not statistically stable. This problem can be solved by starting to omit the variable with largest SE and continuing the process until the magnitude of the SEs are around 0.001-5.0. There is no fixed criterion on how small the SE should be but it is a matter of judgment.

In Table 12, the SEs are within the acceptable criterion but there is a high correlation between age and the constant. However, it is best to keep the constant term in the model as it acts as a "garbage bin", collecting all unexplained variance in the model (see, Table 11. The variables only explain 50%).

TABLE 17

Model discrimination
Classification table[a]

|  |  |  | Predicted | | |
|---|---|---|---|---|---|
|  |  |  | SBP ≥180 | | |
|  | Observed |  | no | yes | Percentage correct |
| Step 1 | SBP ≥180 | No | 38 | 2 | 95.0 |
|  |  | yes | 6 | 9 | 60.0 |
|  | Overall percentage |  |  |  | 85.5 |

[a]The cut value is .500

The logistic model can be used to predict the outcome for a specific individual. The overall accuracy of this particular model to predict subjects having SBP ≥180 (with a predicted probability of 0.5 or greater) is 85.5% (Table 17). The sensitivity is given by 9/15=60% and the specificity is 38/40=95%. Positive predictive value (PPV)=9/11=81.8% and negative predictive value (NPV)=38/44=86.4%.

Figure 7:
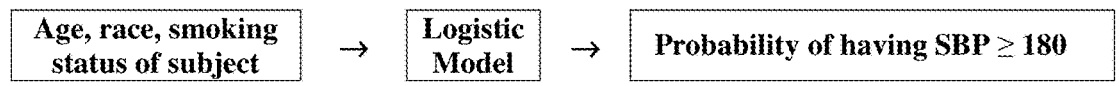
FIG. 7 shows the process of going from data from an individual to predicting the probability of that individual have a medical event.

This logistic model allows the prediction for an individual to have a SBP ≥180 with a certain probability. The age, smoking status and race of the individual is input into a Logistic Model and the output is a number between 0 to 1 which denotes the probability of the subject having SBP ≥180 (FIG. 7).

The Logistic Model equation calculates the probability of having SBP ≥180 which is given by:

$$Prob(SBP \geq 180) = \frac{1}{1 + e^{-z}}$$

where e denotes the exponential function and z=[−14.462]+[0.209*Age]+[2.292*Smoker(1)]+[0.640*Race(1)]+[1.303*Race(2)]−[0.097*Race(3)]. The numerical values are obtained from the B estimates in Table 12.

For example, a 45-year-old non-smoking Chinese would be Smoker(1)=Race(1)=Race(2)=Race(3)=0, and z=[−14.462]+[0.209*45]=−5.057 and $e^{-z}$=157.1 which gives the Prob (SBP ≥180)=1/(1+157.1)=0.006. This shows that it is unlikely that this person has SBP ≥180 and the NPV gives an 86.4% confidence of this prediction being correct.

Another example, a 65-year-old Indian smoker would be Smoker(1)=1, Race(2)=Race(3)=0 but Race(1)=1. Hence z=[−14.462]+[0.209*65]+[2.292*1]+[0.64*1]=2.055 and $e^{-z}$=0.128, which gives the Prob (SBP ≥180)=1/(1+0.128)=0.89. This shows that this individual probability has a SBP ≥180 and the PPV gives an 81.8% confidence of this prediction being correct.

The default cut-off probability is 0.5 (and for this model, this cut-off gives good results). Different probability cutoffs can be used and then tabulate the respective sensitivity, specificity, PPV and NPV, to decide which is the best cut-off for optimal results.

The area under a Receiver Operating Characteristic (ROC) curve, which ranges from 0 to 1, could be used to assess the model discrimination. A value of 0.5 means that the model is useless for discrimination (equivalent to tossing a coin) and values near 1 means that higher probabilities will be assigned to cases with the outcome of interest compared to cases without the outcome. To generate an ROC, the predicted probabilities from the model must be saved.

Figure 8:
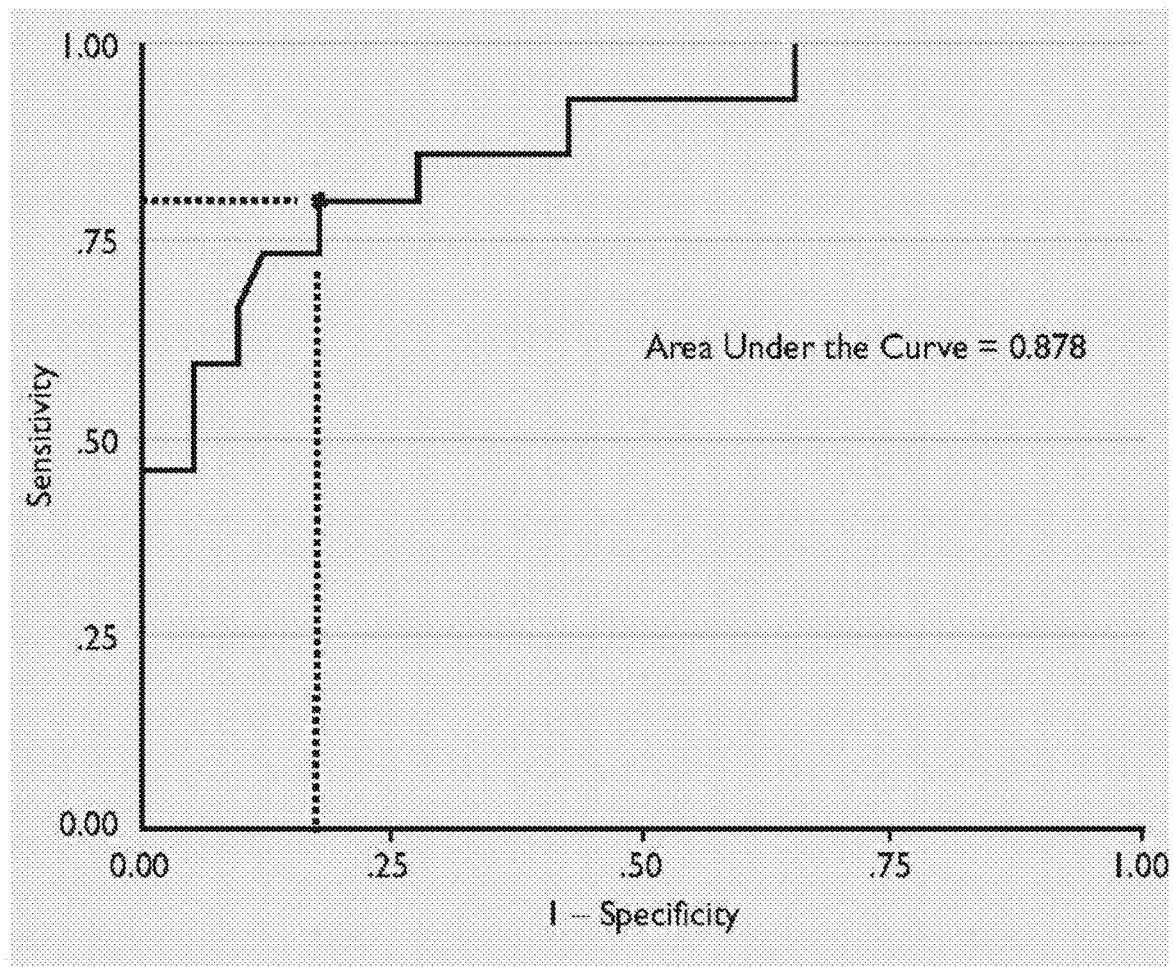
FIG. 8 shows a typical Receiver Operating Characteristic (ROC) curve.

The ROC area for this model is 0.878 (FIG. 8), which means that in almost 88% of all possible pairs of subjects in which one has SBP≥180 and the other SBP<180, this model will assign a higher probability to the subject with SBP ≥180. The optimal sensitivity/specificity is obtained from the point nearest to the left upper corner of the graph. Thus the optimal sensitivity=78% and specificity=1−0.18=82%. Hosmer-Lemeshow goodness of fit will show how closely the observed and predicted probabilities match. The null hypothesis is "the model fits" and a p value >0.05 is expected (Table 18). Caution has to be exercised when using this test as it is dependent on the sample size of the data. For a small sample size, this test will likely indicate that the model fits and for a large dataset, even if the model fits, this test may "fail".

TABLE 18

Hosmer-Lemeshow Test

| Step | Chi-square | df | Sig. |
|---|---|---|---|
| 1 | 5,869 | 7 | 0.555 |

This example covers the situation where the response outcome has only two levels. There are times when it is not possible to collapse the outcome of interest into two groups, for example stage of cancer. There are also situations where the study is a matched case-control.

Thus, although the disclosed systems, processes, methods and apparatuses have been described and illustrated with a certain degree of particularity, it is understood that the present disclosure has been made only by way of example, and that numerous changes in the combination and arrangement of steps, ingredients, or processes can be resorted to by those skilled in the art without departing from the spirit and scope of the disclosed systems, processes, methods and apparatuses, as will be claimed hereafter.

The invention claimed is:

1. A method of determining the effect of ingested compounds on the activity of an anti-coagulant drug in an individual human patient with a hypercoagulable condition and treatment thereof comprising:
    a) obtaining a blood sample from a human patient with a hypercoagulable condition;
    b) detecting an observed International Normalized Ratio (INR) for the human patient with the hypercoagulable condition;
    c) obtaining data of general information of the individual human patient with a hypercoagulable condition comprising:
        current average daily dose of an anti-coagulant drug in milligrams,
        percent compliance of taking the anti-coagulant drug,
        the individual human patient's weight,
        the individual human patient's temperature,
        number of episodes of fevers,
        number of episodes of diarrhea,
        kidney function,
        liver function,
        number of bleeding episodes since last visit, and
        number of clotting episodes since last visit;
    d) obtaining data concerning ingested compounds by the individual human patient with a hypercoagulable condition comprising:
        amount and type of alcohol ingested,
        current prescription drugs, including dosage, frequency and route of intake, and
        amount and type of Vitamin K containing food eaten, and any change in the intake of these foods,
    e) generating and assigning a regression coefficient (($3$) for each data (x) in step c) and step d);
    wherein logistic function is $$Y = \frac{1}{1+e^{-z}}$$

and wherein variable z represents the exposure to independent variables, variable Y represents the probability of a particular outcome, and variable z is defined as:

$$z = \beta_o + \beta_1 x_1 + \beta_2 x_2 + \beta_3 x_3 + \ldots + \beta_n x_n$$

f) using each $\beta_n X_n$ from step e) to represent a predicted relationship between dose amount of the anti-coagulant drug and a predicted INR between 2 and 3 in the individual human patient with a hypercoagulable condition;
    g) modifying each regression coefficient ($\beta_n$) for each data ($x_n$) until the mathematical model program generates an equation of a line representing the predicted relationship between the dose amount of the anti-coagulant drug and the predicted INR which corresponds to the observed INR in the individual human patient with a hypercoagulable condition; and
    h) administering a treatment to the human patient with the hypercoagulable condition, wherein the treatment is the dose amount of the anti-coagulant drug calculated from the equation of the line representing the relationship between the dose amount of the anti-coagulant drug and the predicted INR, and wherein the anti-coagulant drug is selected from the group consisting of Warfarin, Coumadin, Jantoven, Marevan, Lawarin, Waran, Warfant and heparin.

2. The method of claim 1, further comprising the step of obtaining the INR of the individual human patient during a successive visit.

3. The method of claim 2, comprising the steps of:
    comparing the predicted INR with the computer using a mathematical model program selected from the group consisting of a logistic algorithm, multiple linear regression and logistic regression with the observed INR, and
    modifying each regression coefficient ($\beta_n$) for each data ($x_n$) with the computer using a mathematical model program selected from the group consisting of a logistic algorithm, multiple linear regression and logistic regression until the mathematical model program generates a modified regression coefficient ($\beta_n$) for an equation of a line representing the relationship between the dose amount of the anti-coagulant drug and the observed INR in the individual human patient.

4. The method of claim 3, further comprising:
using the modified regression coefficient ($\beta_n$) to generate an equation of a line representing the relationship between the dose amount of the anti-coagulant drug and the INR in the individual human patient in subsequent calculations predicting INR.

5. The method of claim 1, further comprising in step c) obtaining the data of general information of the individual human patient comprising at least one selected from the group consisting of:
the individual human patient's genetic information concerning anticoagulant therapy,
the individual human patient's race,
the individual human patient's age,
the individual human patient's gender,
menopausal status of an individual female,
if the individual human patient is a vegetarian,
if the individual human patient is a vegan,
occurrence and duration of travel since previous visit,
occurrences of trauma since previous visit,
number of falls since last visit,
use of an illegal drug and if yes, the type, frequency and duration of illegal drug use,
intake of dietary supplements,
intake of over the counter medications,
intake of herbal, botanical and alternative medications,
type, frequency and duration of physical exercise,
any change in altitude since previous visit,
any change in time zone since previous visit, and
any change in duration or frequency of sleep since previous visit.

6. The method of claim 5, wherein the herbal medication is selected from the group consisting of Bromelains, Chamomile (*Matricaria recutita*), Coenzyme $Q_{10}$, Cranberry products, Danshen, Dong quai, Echinacea (*Echinacea* purpurea and *Echinacea* spp.), Evening Primrose (*Oenothera biennis*), Feverfew (*Tanacetum parthenium*), Garlic (*Allium sativum*), Ginger (*Zingiber officinale*), Ginkgo (*Ginkgo biloba*), Ginseng (*Panax* spp.), Goldenseal (Hydrastis *canadensis*), Kava Kava (*Piper methysticum*), Milk Thistle (*Silybum marianum*), Saw Palmetto (Serenoa *repens*), St. John's Wort (*Hypericum* perforatum), and Valerian (Valeriana *officinalis*).

7. The method of claim 5, wherein the over the counter drugs are selected from the group consisting of antibiotics, aspirin, aspirin-containing products, nonsteroidal anti-inflammatory drugs, ibuprofen, naproxen, oral contraceptives, streptokinase, ticlopidine, and urokinase; and medications for cancer, cholesterol, colds, allergies, depression, diabetes, digestive problems, gout, heart disease, mental illness, pain, seizures, thyroid problems and tuberculosis.

8. The method of claim 1, wherein steps a) to d) are repeated during each visit by the individual human patient.

9. The method of claim 1, wherein the mathematical model is logistic regression.

10. The method of claim 1, wherein the equation of a line in step g) is a general model generated by data from multiple people.

11. The method of claim 1, wherein the equation of a line in step g) is a model generated for the specific individual human patient.

12. The method of claim 1, wherein the mathematical model has a variable "z," and wherein the z is generated by a logistic regression model.

13. The method of claim 12, wherein the z generated by the logistic regression model is averaged between a population of individual human patients to generate an averaged z and the averaged z is used as the initial z for a human patient without an individual mathematical model.

14. The method of claim 1, wherein the data are stored in a data base for that individual human patient.

15. The method of claim 1, wherein the data are recorded in digital form with "1" representing "yes" or "present" and "0" representing "no" or "absent".

16. The method of claim 1, wherein the anti-coagulant drug is Warfarin.

17. The method of claim 1, wherein the prescription drugs are selected from the group consisting of antibiotics, aspirin, aspirin-containing products, nonsteroidal anti-inflammatory drugs, ibuprofen, naproxen, oral contraceptives, streptokinase, ticlopidine, and urokinase; and medications for cancer, cholesterol, colds, allergies, depression, diabetes, digestive problems, gout, heart disease, mental illness, pain, seizures, thyroid problems and tuberculosis.

18. The method of claim 1, wherein the computer using a mathematical model program selected from the group consisting of a logistic algorithm, multiple linear regression and logistic regression is a hand-held device.

19. The method of claim 1, wherein the hypercoagulable condition is selected from the group consisting of atrial fibrillation, prosthetic heart valve, blood clots, pulmonary emboli and deep venous thromboses.

* * * * *